United States Patent
Greco et al.

(10) Patent No.: US 8,476,302 B2
(45) Date of Patent: Jul. 2, 2013

(54) α-KETOAMIDE DERIVATIVES USEFUL ENDOTHELIAL LIPASE INHIBITORS

(75) Inventors: Michael N. Greco, Spring House, PA (US); Margery A. Connelly, Lansdale, PA (US); Shyamali Ghosh, Norristown, PA (US); Dennis J. Hlasta, Doylestown, PA (US); Edward C. Lawson, Pipersville, PA (US); Eric Strobel, Warrington, PA (US); Michele A. Weidner-Wells, Doylestown, PA (US); Hong Ye, Lansdale, PA (US)

(73) Assignee: Janssen Pharmaceutica N.V. (BE)

( * ) Notice: Subject to any disclaimer, the term of this patent is extended or adjusted under 35 U.S.C. 154(b) by 7 days.

(21) Appl. No.: 13/245,137

(22) Filed: Sep. 26, 2011

(65) Prior Publication Data

US 2012/0077847 A1    Mar. 29, 2012

Related U.S. Application Data

(60) Provisional application No. 61/386,671, filed on Sep. 27, 2010.

(51) Int. Cl.
*A61K 31/4245* (2006.01)
*A61K 31/4439* (2006.01)
*A61K 31/433* (2006.01)
*C07D 285/12* (2006.01)
*C07D 417/12* (2006.01)
*C07D 271/107* (2006.01)

(52) U.S. Cl.
USPC ........... 514/342; 514/364; 514/363; 548/143; 548/136; 546/268.7

(58) Field of Classification Search
None
See application file for complete search history.

(56) References Cited

U.S. PATENT DOCUMENTS 5,278,326 A    1/1994 Augelli-Szafran et al.
2005/0107616 A1    5/2005 Barrett et al.

OTHER PUBLICATIONS

International Search Report, PCT/US 11/53236, Dated Feb. 14, 2012.
Ma, et al., "Endothelial Lipase is a Major Genetic Determinant for High-Density Lipoprotein Concentration, Structure, and Metabolism" Proceedings in the National Academy of Science, 2003, pp. 2748-2753, vol. 100.

*Primary Examiner* — Yong Chu
(74) *Attorney, Agent, or Firm* — Yuriy P. Stercho

(57) ABSTRACT

The present invention is directed to α-ketoamide derivatives, pharmaceutical compositions containing them and their use in the treatment of disorders and conditions modulated by endothelial lipase, for example, cardiovascular disorders.

17 Claims, No Drawings

α-KETOAMIDE DERIVATIVES USEFUL ENDOTHELIAL LIPASE INHIBITORS

CROSS REFERENCE TO RELATED APPLICATIONS

This application claims the benefit of U.S. Provisional Application 61/386,671, filed on Sep. 27, 2010, which is incorporated by reference herein in its entirety.

FIELD OF THE INVENTION

The present invention is directed to α-ketoamide derivatives, pharmaceutical compositions containing them and their use in the treatment of disorders and conditions modulated by endothelial lipase. More particularly, the compounds of the present invention are endothelial lipase inhibitors, useful in the treatment of cardiovascular disorder.

BACKGROUND OF THE INVENTION

Endothelial lipase (EL), a serine-phospholipase, is a member of the triglyceride lipase family first cloned in 1999. Unlike other triglyceride lipases, EL has a dramatic difference in substrate preference, possessing predominantly phospholipase activity rather than triglyceride lipase activity. Importantly, a role for EL in the regulation of HDL cholesterol in mice has been well-documented. EL knockout mice have a pronounced elevation in HDL cholesterol relative to wild type mice. Moreover, recent studies suggest that EL may have a pro-inflammatory effect and may be involved in atherogenesis. Taken together, this evidence suggests that an EL inhibitor could have benefit in the treatment of cardiovascular disease.

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors. Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis.

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol. Endothelial lipase (also known as EDL, EL, LIPG, endothelial-derived lipase, and endothelial cell-derived lipase) is synthesized in endothelial cells, a characteristic that distinguishes it from the other members of the family. At least 50% of the variation in HDL cholesterol levels is genetically determined.

The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects. Notably, the endothelial lipase-mediated binding and uptake of HDL particles and the selective uptake of HDL-derived cholesterol esters have been reported to be independent of its enzymatic lipolytic activity. Recombinant endothelial lipase protein has substantial phospholipase activity but has been reported to have less hydrolytic activity toward triglyceride lipids. However, endothelial lipase does exhibit triglyceride lipase activity ex vivo in addition to its HDL phospholipase activity, and endothelial lipase was found to hydrolyze HDL more efficiently than other lipoproteins. Over expression of the human endothelial lipase gene in the livers of mice markedly reduces plasma concentrations of HDL cholesterol and its major protein apolipoprotein A-I (apoA-I).

There remains a need for compounds that can inhibit lipase, more particularly endothelial lipase, for the treatment of, for example, cardiovascular disorders.

SUMMARY OF THE INVENTION

The present invention is directed to compounds of formula (I)

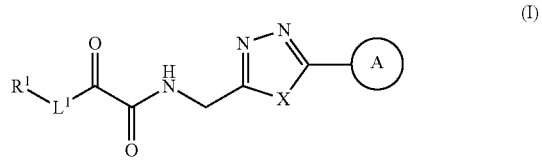

wherein $R^1$ is an aromatic ring selected from the group consisting of phenyl, pyridyl, pyrimidinyl, thiazolyl, and quinolinyl;

wherein the aromatic ring is optionally substituted with one to two substituents independently selected from the group consisting of halogen, $C_{1-4}$alkyl, trifluoromethyl, $C_{1-4}$alkoxy, trifluoromethoxy, cyano, —C(O)—$NR^A R^B$, —NH—C(O)—($C_{1-4}$alkyl), and phenyl; and wherein $R^A$ and $R^B$ are each independently selected from the group consisting of hydrogen and $C_{1-4}$alkyl;

$L^1$ is selected from the group consisting of -(n-pentyl)-, -(n-hexyl)-, —O-(n-pentyl)-, —NH-(n-pentyl)-, —CH=CH-(n-propyl)-, —CH=CH-(n-butyl)-, —CC-(n-propyl)- and —CC-(n-butyl)-; (wherein the $L^1$ group is incorporated into the structure in the orientation listed)

X is selected from the group consisting of —NH—, —O— and —S—;

is selected from the group consisting of
(a)

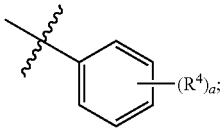

a is an integer from 0 to 2;

each $R^4$ is independently selected from the group consisting of halogen, $C_{1-4}$alkyl, trifluoromethyl, $C_{1-4}$alkoxy, trifluoromethoxy, $NR^6R^7$, —C(O)—NH—CH$_2$CH$_2$—NR$^6$R$^7$ and phenyl; wherein $R^6$ and $R^7$ are each independently selected form the group consisting of hydrogen and $C_{1-4}$alkyl;

wherein the $R^4$ phenyl is optionally substituted with one to three substituents independently selected from the group consisting of halogen, $C_{1-4}$alkyl, trifluoromethyl, $C_{1-4}$alkoxy and trifluoromethoxy;

(b)

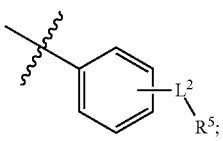

$L^2$ is selected from the group consisting of —O—, —NR$^7$— and —S(O)—; wherein $R^7$ is selected from the group consisting of hydrogen, $C_{1-4}$alkyl and t-butoxycarbonyl;

$R^5$ is an aromatic ring structure selected from the group consisting of phenyl, benzyl, phenylethyl-, imidazolyl, imidazolyl-methyl-, pyridyl, pyridyl-methyl-, pyrimidinyl, pyrimidinyl-methyl-, furyl, furyl-methyl-, quinolinyl, quinolinyl-methyl-, benzo[d][1,2,3]triazolyl and benzo[d][1,2,3]triazolyl-methyl-;

wherein the $R^5$ aromatic ring structure is optionally substituted with one to two substituents independently selected from the group consisting of halogen, $C_{1-4}$alkyl, trifluoromethyl, $C_{1-4}$alkoxy, trifluoromethoxy, —C(O)OH, —C(O)—O—$C_{1-4}$alkyl, cyano, and —C(O)—NR$^8$R$^9$; wherein R$^8$ and R$^9$ are each independently selected from the group consisting of hydrogen and $C_{1-4}$alkyl;

alternatively $R^5$ is 4-(pyrid-4-yl-N-oxide-methoxy)-phenyl;

and wherein the -L$^2$-R$^5$ group is bound at the 3- or 4-position;

(c) naphth-2-yl; and (d) a heteroaryl selected from the group consisting of pyridyl, benzo[d][1,3]dioxolyl, dibenzo[b,e][1,4]dioxinyl, and 2,3-dihydropyrrolo[2,1-b]quinazolin-9-one;

and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by endothelial lipase (selected from the group consisting of atherosclerosis, dyslipidemia, low HDL and high LDL) in a subject in need thereof comprising administering to the subject a therapeutically effective amount of any of the compounds or pharmaceutical compositions described above.

Another example of the invention is the use of any of the compounds described herein in the preparation of a medicament for treating: (a) atherosclerosis, (b) dyslipidemia, (c) low HDL or (d) high LDL, in a subject in need thereof.

DETAILED DESCRIPTION OF THE INVENTION

The present invention is directed to compounds of formula (I)

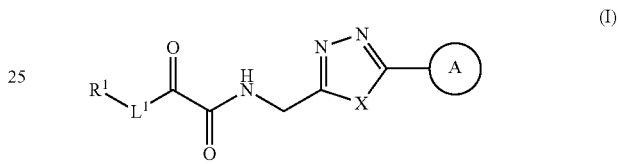

wherein $R^1$, $L^1$, X and

are as herein defined, and pharmaceutically acceptable salts thereof. The compounds of the present invention are endothelial lipase inhibitors, useful in the treatment of cardiovascular disorders including, but not limited to, atherosclerosis, dyslipidemia, low HDL, high LDL, and the like, preferably atherosclerosis or dyslipidemia. The compounds of formula (I) of the present invention were further found to be selective for inhibition of EL (endothelial lipase) over inhibition of LPL (lipoprotein lipase). The compounds of formula (I) of the present invention are therefore preferred over non-selective EL inhibitors, as inhibition of LPL can lead to the undesired effect of increased triglyceride levels.

In an embodiment, the present invention is directed to compounds of formula (I) wherein $R^1$ is an aromatic ring selected from the group consisting of phenyl, pyridyl, pyrimidinyl, thiazolyl, and quinolinyl; wherein the aromatic ring is optionally substituted with one to two substituents independently selected from the group consisting of halogen, $C_{1-4}$alkyl, trifluoromethyl, $C_{1-4}$alkoxy, trifluoromethoxy, cyano, —C(O)—NR$^A$R$^B$, —NH—C(O)—($C_{1-4}$alkyl) and phenyl; and wherein $R^A$ and $R^B$ are each independently selected from the group consisting of hydrogen and $C_{1-2}$alkyl. In another embodiment, the present invention is directed to compounds of formula (I) wherein $R^1$ is an aromatic ring selected from the group consisting of phenyl, pyridyl, pyrimidinyl, thiazolyl and quinolinyl; wherein the aromatic ring is optionally substituted with one to two substituents independently selected from the group consisting of halogen, $C_{1-2}$alkyl, trifluoromethyl, $C_{1-2}$alkoxy, cyano, —C(O)—NH$_2$, —NH—C(O)—($C_{1-2}$alkyl) and phenyl.

In another embodiment, the present invention is directed to compounds of formula (I) wherein R¹ is selected from the group consisting of phenyl, 3-methoxy-phenyl, 4-methoxy-phenyl, 2-fluoro-phenyl, 3-fluoro-phenyl, 4-fluoro-phenyl, 3-chloro-phenyl, 4-cyano-phenyl, 3-trifluoromethyl-phenyl, 2,3-difluoro-phenyl, 2,4-difluoro-phenyl, 2,5-difluoro-phenyl, 2,6-difluoro-phenyl, 3,5-difluoro-phenyl, 4-biphenyl, pyrid-4-yl, 2-fluoro-pyrid-3-yl, 6-fluoro-pyrid-2-yl, 6-fluoro-pyrid-3-yl, 6-trifluoromethyl-pyrid-3-yl, 5-aminocarbonyl-pyrid-3yl, 6-(methylcarbonylamino)-pyrid-3-yl, pyrimidin-2-yl, 4-methyl-thiazol-5-yl and 2-chloro-quinolin-6-yl.

In another embodiment, the present invention is directed to compounds of formula (I) wherein R¹ is selected from the group consisting of phenyl, 3-methoxy-phenyl, 3-fluoro-phenyl, 4-fluoro-phenyl, 2,4-difluoro-phenyl, 3,5-difluoro-phenyl, 6-fluoro-pyrid-3-yl, 6-(methylcarbonylamino)-pyrid-3-yl and 4-methyl-thiazol-5-yl. In another embodiment, the present invention is directed to compounds of formula (I) wherein R¹ is selected from the group consisting of phenyl, 3-methoxy-phenyl, 3-fluoro-phenyl, 6-fluoro-pyrid-3-yl and 4-methyl-thiazol-5-yl. In another embodiment, the present invention is directed to compounds of formula (I) wherein R¹ is selected from the group consisting of phenyl, 6-fluoro-pyrid-3-yl and 4-methyl-thiazol-5-yl. In another embodiment, the present invention is directed to compounds of formula (I) wherein R¹ is selected from the group consisting of phenyl, 6-fluoro-pyrid-3-yl and 4-methyl-thiazol-5-yl.

In an embodiment, the present invention is directed to compounds of formula (I) wherein L¹ is selected from the group consisting of -(n-pentyl), -(n-hexyl)-, —O-(n-pentyl)-, —NH-(n-pentyl)-, —CH═CH-(n-butyl)-, —CC-(n-propyl)- and —CC-(n-butyl)-. In another embodiment, the present invention is directed to compounds of formula (I) wherein L¹ is selected from the group consisting of -(n-pentyl)-, -(n-hexyl)-, —O-(n-pentyl)-, —NH-(n-pentyl)-, —CH═CH-(n-butyl)-, —CC-(n-propyl)- and —CC-(n-butyl)-. In another embodiment, the present invention is directed to compounds of formula (I) wherein L¹ is selected from the group consisting of -(n-pentyl)-, -(n-hexyl)-, —O-(n-pentyl)-, —NH-(n-pentyl)-, —CH═CH-(n-butyl)-, —CC-(n-propyl)- and —CC-(n-butyl)-. In another embodiment, the present invention is directed to compounds of formula (I) wherein L¹ is selected from the group consisting of -(n-hexyl)- and —O-(n-pentyl)-. In another embodiment, the present invention is directed to compounds of formula (I) wherein L¹ is -(n-hexyl)-.

In an embodiment, the present invention is directed to compounds of formula (I) wherein X is selected from the group consisting of O and S. In another embodiment, the present invention is directed to compounds of formula (I) wherein X is selected from the group consisting of O and NH. In another embodiment, the present invention is directed to compounds of formula (I) wherein X is O. In another embodiment, the present invention is directed to compounds of formula (I) wherein X is NH. In another embodiment, the present invention is directed to compounds of formula (I) wherein X is S.

In an embodiment, the present invention is directed to compounds of formula (I) wherein (A)

is (a)

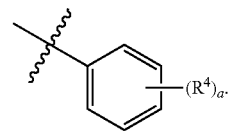

In another embodiment, the present invention is directed to compounds of formula (I) wherein (A)

is (b)

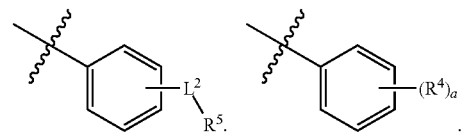

In another embodiment, the present invention is directed to compounds of formula (I) wherein (A)

is

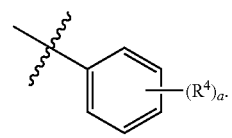

In another embodiment, the present invention is directed to compounds of formula (I) wherein (A)

is (c) naphth-2-yl.

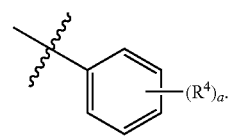

In another embodiment, the present invention is directed to compounds of formula (I) wherein (A)

is (d) a heteroaryl selected from the group consisting of pyridyl, benzo[d][1,3]dioxolyl, dibenzo[b,e][1,4]dioxinyl, and 2,3-dihydropyrrolo[2,1-b]quinazolin-9-one.

In an embodiment, the present invention is directed to compounds of formula (I) wherein

is selected from the group consisting of
(a)

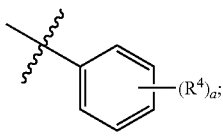

wherein a is an integer from 0 to 2; and each $R^4$ is independently selected from the group consisting of halogen, $C_{1-4}$alkyl, trifluoromethyl, $C_{1-4}$alkoxy, trifluoromethoxy, —$NR^6R^7$, —C(O)—NH—$CH_2CH_2$—$NR^6R^7$ and phenyl; wherein $R^6$ and $R^7$ are each independently selected from the group consisting of hydrogen and $C_{1-4}$alkyl;
(b)

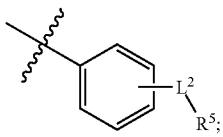

wherein $L^2$ is selected from the group consisting of —O—, —$NR^7$— and —S(O)—; wherein $R^7$ is selected from the group consisting of hydrogen, $C_{1-4}$alkyl and t-butoxycarbonyl; and $R^5$ is an aromatic ring structure selected from the group consisting of phenyl, benzyl, phenylethyl-, imidazolyl-methyl-, pyridyl-methyl-, pyrimidinyl-methyl-, furyl-methyl-, quinolinyl-methyl- and benzo[d][1,2,3]triazolyl-methyl-; wherein the $R^5$ aromatic ring structure is optionally substituted with one to two substituents independently selected from the group consisting of halogen, $C_{1-4}$alkyl, trifluoromethyl, $C_{1-4}$alkoxy, trifluoromethoxy, —C(O)OH, —C(O)—O—$C_{1-4}$alkyl, cyano, and —C(O)—$NR^8R^9$; wherein $R^8$ and $R^9$ are each independently selected from the group consisting of hydrogen and $C_{1-4}$alkyl; alternatively $R^5$ is 4-(pyrid-4-yl-N-oxide-methoxy)-phenyl; and wherein the -$L^2$-$R^5$ group is bound at the 3- or 4-position;

(c) naphth-2-yl; and (d) a heteroaryl selected from the group consisting of pyridyl, benzo[d][1,3]dioxolyl, dibenzo[b,e][1,4]dioxinyl and 2,3-dihydropyrrolo[2,1-b]quinazolinone.

In another embodiment, the present invention is directed to compounds of formula (I) wherein

is selected from the group consisting of
(a)

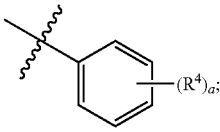

wherein a is an integer from 0 to 2; and wherein each $R^4$ is independently selected from the group consisting of halogen, $C_{1-2}$alkyl, trifluoromethyl, $C_{1-2}$alkoxy, —$NR^6R^7$, —C(O)—NH—$CH_2CH_2$—$NR^6R^7$ and phenyl; wherein $R^6$ and $R^7$ are each independently selected from the group consisting of hydrogen and $C_{1-2}$alkyl;
(b)

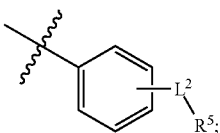

wherein wherein $L^2$ is selected from the group consisting of —O—, —$NR^7$— and —S(O)—; wherein $R^7$ is selected from the group consisting of hydrogen, $C_{1-2}$alkyl and t-butoxycarbonyl; and $R^5$ is an aromatic ring structure selected from the group consisting of phenyl, benzyl, phenylethyl-, imidazolyl-methyl-, pyridyl-methyl-, pyrimidinyl-methyl-, furyl-methyl-, quinolinyl-methyl- and benzo[d][1,2,3]triazolyl-methyl-; wherein the $R^5$ aromatic ring structure is optionally substituted with one to two substituents independently selected from the group consisting of halogen, $C_{1-2}$alkyl, $C_{1-2}$alkoxy, —C(O)OH, —C(O)O—$C_{1-4}$alkyl, cyano, and —C(O)—$NR^8R^9$; wherein $R^8$ and $R^9$ are each independently selected from the group consisting of hydrogen and $C_{1-2}$alkyl; alternatively $R^5$ is 4-(pyrid-4-yl-N-oxide-methoxy)-phenyl; and wherein the -$L^2$-$R^5$ group is bound at the 3- or 4-position;

(c) naphth-2-yl; and (d) a heteroaryl selected from the group consisting of pyridyl, benzo[d][1,3]dioxol-5-yl, dibenzo[b,e][1,4]dioxin-2-yl and 6-(2,3-dihydropyrrolo[2,1-b]guinazolin-9-one);

In another embodiment, the present invention is directed to compounds of formula (I) wherein

is selected from the group consisting of
(a) phenyl, 2-fluoro-phenyl, 3-fluoro-phenyl, 4-fluoro-phenyl, 3,4-difluoro-phenyl, 3,5-difluoro-phenyl, 2-chloro-phenyl, 3-chloro-phenyl, 4-chlorophenyl, 4-methyl-phenyl, 2-methoxy-phenyl, 3-methoxy-phenyl, 4-methoxy-phenyl, 3-trifluoromethyl-phenyl, 4-trifluoromethyl-phenyl, 4-dimethylamino-phenyl and 4-(dimethylamino-ethylamino-carbonyl)-phenyl;

(b) 3-phenoxy-phenyl, 4-phenoxy-phenyl, 4-(3-chlorophenoxy)-phenyl, 4-(4-chloro-phenoxy)-phenyl, 4-(4-fluoro-phenoxy)-phenyl, 4-benzyloxy-phenyl, 4-(2-fluorobenzyloxy)-phenyl, 4-(3-fluoro-benzyloxy)-phenyl, 4-(4-fluoro-benzyloxy)-phenyl, 4-(3,5-difluoro-benzyloxy)-phenyl, 4-(4-methoxy-benzyloxy)-phenyl, 4-(3-cyanobenzyloxy)-phenyl, 4-(3-carboxy-benzyloxy)-phenyl, 4-(3-methoxycarbonyl-benzyloxy)-phenyl, 4-(3-t-butoxycarbonyl-benzyloxy)-phenyl, 4-(3-dimethylamino-carbonyl-benzyloxy)-phenyl, 4-(phenyl-ethoxy)-phenyl, 4-(N-methyl-N-(4-bromophenyl)-amino)-phenyl, 4-(N-benzyl-amino)-phenyl, 4-(N-methyl-N-benzyl-amino)-phenyl, 4-(N-(3,4-difluorobenzyl)-amino)-phenyl, 4-(N-methyl-N-(3,4-difluorobenzyl)-amino)-phenyl, 4-(N-methyl-N-(pyrid-2-ylmethyl)-amino)-phenyl, 4-(N-benzyl-N-4-butoxycarbonyl)-amino)-phenyl, 4-(N-(3,4-difluorobenzyl)-amino)-phenyl, 4-(N-(pyrid-3-yl-methyl)-amino)-phenyl, 4-(N-t-butoxycarbonyl-N-(pyrid-3-yl-methyl)amino)-phenyl, 4-(pyrid-2-yl-methoxy)-phenyl, 4-(pyrid-3-yl-methoxy)-phenyl, 4-(pyrid-4-yl-methoxy)-phenyl, 4-(2-fluoro-pyrid-2-yl-methoxy)-phenyl, 4-(3-fluoro-pyrid-2-yl-methoxy)phenyl, 4-(6-fluoro-pyrid-2-yl-methoxy)-phenyl, 4-(6-chloro-pyrid-2-yl-methoxy)-phenyl, 4-(3-fluoro-pyrid-4-yl-methoxy)-phenyl, 4-(5-fluoro-pyrid-3-yl-methoxy)-phenyl, 4-(2-fluoro-pyrid-4-yl-methoxy)-phenyl, 4-(2-chloro-pyrid-4-yl-methoxy)-phenyl, 4-(3-fluoro-pyrid-4-yl-methoxy)-phenyl, 4-(2,6-dichloro-pyrid-4-yl-methoxy)-phenyl, 4-(6-bromo-pyrid-2-yl-methoxy)-phenyl, 4-(2-methyl-pyrid-4-yl-methoxy)-phenyl, 4-(6-cyano-pyrid-2-yl-methoxy)-phenyl, 4-(1-methyl-imidazol-2-yl-methoxy)-phenyl, 4-(pyrimidin-2-yl-methoxy)-phenyl, 4-(pyrimidin-4-yl-methoxy)-phenyl, 4-(quinolin-2-yl-methoxy)-phenyl, 4-(5-methoxycarbonyl-fur-2-yl-methoxy)-phenyl, 4-(1H-benzo[d]1,2,3]triazol-1-yl-methoxyl)-phenyl, 4-(benzyl-sulfonyl)-phenyl, 4-(pyrid-4-yl-N-oxide-methoxy)-phenyl;

(c) naphth-2-yl; and (d) pyrid-3-yl, pyrid-4-yl, benzo[d][1,3]dioxol-5-yl, dibenzo[b,e][1,4]dioxin-2-yl and 6-(2,3-dihydropyrrolo[2,1-b]quinazolin-9-one).

In another embodiment, the present invention is directed to compounds of formula (I) wherein (A)

is selected from the group consisting of
(a) phenyl, 3,4-difluoro-phenyl, 3-chloro-phenyl, 4-chloro-phenyl, 4-methyl-phenyl and 4-trifluoromethyl-phenyl;
(b) 4-phenoxy-phenyl, 4-(3-chloro-phenoxy)-phenyl, 4-benzyloxy-phenyl, 4-(2-fluoro-benzyloxy)-phenyl, 4-(3-fluoro-benzyloxy)-phenyl, 4-(3,5-difluoro-benzyloxy)-phenyl, 4-(3-cyano-benzyloxy)-phenyl, 4-(3-methoxycarbonyl-benzyloxy)-phenyl, 4-(3-dimethylamino-carbonyl-benzyloxy)-phenyl, 4-(phenyl-ethoxy)-phenyl, 4-(N-benzyl-amino)-phenyl, 4-(N-methyl-N-benzyl-amino)-phenyl, 4-(N-methyl-N-(pyrid-2-ylmethyl)-amino)-phenyl, 4-(N-benzyl-N-4-butoxycarbonyl)-amino)-phenyl, 4-(N-t-butoxycarbonyl-N-(pyrid-3-yl-methyl)-amino)-phenyl, 4-(pyrid-2-yl-methoxy)-phenyl, 4-(pyrid-3-yl-methoxy)-phenyl, 4-(pyrid-4-yl-methoxy)-phenyl, 4-(6-fluoro-pyrid-2-yl-methoxy)-phenyl, 4-(3-fluoro-pyrid-4-yl-methoxy)-phenyl, 4-(2-fluoro-pyrid-4-yl-methoxy)-phenyl, 4-(2-chloro-pyrid-4-yl-methoxy)-phenyl, 4-(2-methyl-pyrid-4-yl-methoxy)-phenyl, 4-(pyrimidin-4-yl-methoxy)-phenyl, 4-(5-methoxycarbonyl-fur-2-yl-methoxy)-phenyl, 4-(1H-benzo[d]1,2,3]triazol-1-yl-methoxyl)-phenyl, 4-(pyrid-4-yl-N-oxide-methoxy)-phenyl;
(c) naphth-2-yl; and (d) benzo[d][1,3]dioxol-5-yl.

In another embodiment, the present invention is directed to compounds of formula (I) wherein (A)

is selected from the group consisting of (a) phenyl and 4-methyl-phenyl; (b) 4-phenoxy-phenyl, 4-(3-chloro-phenoxy)-phenyl, 4-benzyloxy-phenyl, 4-(2-fluoro-benzyloxy)-phenyl, 4-(3-fluoro-benzyloxy)-phenyl, 4-(3-cyano-benzyloxy)-phenyl, 4-(3-methoxycarbonyl-benzyloxy)-phenyl, 4-(3-dimethylamino-carbonyl-benzyloxy)-phenyl, 4-(phenyl-ethoxy)-phenyl, 4-(N-methyl-N-(pyrid-2-ylmethyl)-amino)-phenyl, 4-(pyrid-2-yl-methoxy)-phenyl, 4-(pyrid-3-yl-methoxy)-phenyl, 4-(pyrid-4-yl-methoxy)-phenyl, 4-(3-fluoro-pyrid-4-yl-methoxy)-phenyl, 4-(2-fluoro-pyrid-4-yl-methoxy)-phenyl, 4-(2-chloro-pyrid-4-yl-methoxy)-phenyl, 4-(2-methyl-pyrid-4-yl-methoxy)-phenyl, 4-(5-methoxycarbonyl-fur-2-yl-methoxy)-phenyl, 4-(1H-benzo[d]1,2,3]triazol-1-yl-methoxy)-phenyl; and (c) naphth-2-yl.

In another embodiment, the present invention is directed to compounds of formula (I) wherein (A)

is selected from the group consisting of (b) 4-phenoxy-phenyl, 4-(3-fluoro-benzyloxy)-phenyl, 4-(3-cyano-benzyloxy)-phenyl, 4-(3-methoxycarbonyl-benzyloxy)-phenyl, 4-(3-dimethylamino-carbonyl-benzyloxy)-phenyl, 4-(pyrid-2-yl-methoxy)-phenyl, 4-(pyrid-3-yl-methoxy)-phenyl, 4-(pyrid-4-yl-methoxy)-phenyl, 4-(3-fluoro-pyrid-4-yl-methoxy)-phenyl, 4-(2-fluoro-pyrid-4-yl-methoxy)phenyl, 4-(2-chloro-pyrid-4-yl-methoxy)-phenyl, 4-(2-methyl-pyrid-4-yl-methoxy)-phenyl and 4-(5-methoxycarbonyl-fur-2-yl-methoxy)-phenyl.

In another embodiment, the present invention is directed to compounds of formula (I) wherein (A)

is selected from the group consisting of (b) 4-(3-fluoro-benzyloxy)-phenyl, 4-(3-methoxycarbonyl-benzyloxy)-phenyl, 4-(pyrid-4-yl-methoxy)-phenyl and 4-(2-chloro-pyrid-4-yl-methoxy)-phenyl.

In an embodiment, the present invention is directed to compounds of formula (I) wherein a is an integer from 0 to 2. In another embodiment, the present invention is directed to compounds of formula (I) wherein a is an integer from 1 to 2.

In an embodiment, the present invention is directed to compounds of formula (I) wherein each $R^4$ is independently selected from the group consisting of halogen, $C_{1-4}$alkyl, trifluoromethyl, $C_{1-4}$alkoxy, trifluoromethoxy, —$NR^6R^7$, —C(O)—NH—$CH_2CH_2$—$NR^6R^7$ and phenyl; wherein $R^6$ and $R^7$ are each independently selected from the group consisting of hydrogen and $C_{1-4}$alkyl. In another embodiment, the present invention is directed to compounds of formula (I) wherein each $R^4$ is independently selected from the group consisting of halogen, $C_{1-2}$alkyl, trifluoromethyl, $C_{1-2}$alkoxy, —$NR^6R^7$, —C(O)—NH—$CH_2CH_2$—$NR^6R^7$ and phenyl; wherein $R^6$ and $R^7$ are each independently selected from the group consisting of hydrogen and $C_{1-2}$alkyl.

In an embodiment, the present invention is directed to compounds of formula (I) wherein $L^2$ is selected from the group consisting of —O—, —NR$^7$— and —S(O)—; wherein $R^7$ is selected from the group consisting of hydrogen, $C_{1-4}$alkyl and t-butoxycarbonyl. In another embodiment, the present invention is directed to compounds of formula (I) wherein $L^2$ is selected from the group consisting of —O—, —NR$^7$— and —S(O)—; wherein $R^7$ is selected from the group consisting of hydrogen, $C_{1-2}$alkyl and t-butoxycarbonyl.

In an embodiment, the present invention is directed to compounds of formula (I) wherein $R^5$ is an aromatic ring structure selected from the group consisting of phenyl, benzyl, phenylethyl-, imidazolyl-methyl-, pyridyl-methyl-, pyrimidinyl-methyl-, furyl-methyl-, quinolinyl-methyl- and benzo[d][1,2,3]triazolyl-methyl-; and wherein the $R^5$ aromatic ring structure is optionally substituted with one to two substituents independently selected from the group consisting of halogen, $C_{1-4}$alkyl, trifluoromethyl, $C_{1-4}$alkoxy, trifluoromethoxy, —C(O)OH, —C(O)—O—$C_{1-4}$alkyl, cyano, and —C(O)—NR$^8$R$^9$; wherein $R^8$ and $R^9$ are each independently selected from the group consisting of hydrogen and $C_{1-4}$alkyl.

In another embodiment, the present invention is directed to compounds of formula (I) wherein $R^5$ is an aromatic ring structure selected from the group consisting of phenyl, benzyl, phenylethyl-, imidazolyl-methyl-, pyridyl-methyl-, pyrimidinyl-methyl-, furyl-methyl-, quinolinyl-methyl- and benzo[d][1,2,3]triazolyl-methyl-; and wherein the $R^5$ aromatic ring structure is optionally substituted with one to two substituents independently selected from the group consisting of halogen, $C_{1-2}$alkyl, $C_{1-2}$alkoxy, —C(O)OH, —C(O)O—$C_{1-4}$alkyl, cyano, and —C(O)—NR$^8$R$^9$; wherein $R^8$ and $R^9$ are each independently selected from the group consisting of hydrogen and $C_{1-2}$alkyl; alternatively $R^5$ is 4-(pyrid-4-yl-N-oxide-methoxy)-phenyl.

In an embodiment, the present invention is directed to compounds of formula (I) wherein the -$L^2$-$R^5$ group is bound at the 3-position. In another embodiment, the present invention is directed to compounds of formula (I) wherein the -$L^2$-$R^5$ group is bound at the 4-position.

Additional embodiments of the present invention, include those wherein the substituents selected for one or more of the variables defined herein (i.e. a, $R^1$, $L^1$, X,

Ⓐ etc.) are independently selected to be any individual substituent or any subset of substituents selected from the complete list as defined herein. In another embodiment of the present invention is any single compound or subset of compounds selected from the representative compounds listed in Tables 1-3 below.

Representative compounds of the present invention are as listed in Table 1 to 3 below. Unless otherwise noted, wherein a stereogenic center is present in the listed compound, the compound was prepared as a mixture of stereo-configurations. Where a stereogenic center is present, the S*— and R* designations are intended to indicate that the exact stereo-configuration of the center has not been determined.

TABLE 1

Representative Compounds of Formula (I)

| ID No | $R^1$ | $L^1$ | X | $(R^4)_a$ |
|---|---|---|---|---|
| 1 | phenyl | -n-hexyl- | O | a = 0 |
| 2 | phenyl | -n-hexyl- | O | 4-chloro |
| 3 | phenyl | -n-hexyl- | O | 3-methoxy |
| 4 | phenyl | -n-hexyl- | O | 4-methoxy |
| 5 | phenyl | -n-hexyl- | O | 2-chloro |
| 6 | phenyl | -n-hexyl- | O | 2-methoxy |
| 11 | phenyl | -n-hexyl- | NH | a = 0 |
| 12 | phenyl | -n-hexyl- | O | 2-fluoro |
| 13 | phenyl | -n-hexyl- | O | 3-fluoro |
| 15 | phenyl | -n-hexyl- | O | 4-fluoro |
| 17 | phenyl | -n-hexyl- | O | 4-phenyl |
| 18 | phenyl | -n-hexyl- | O | 3-chloro |
| 20 | phenyl | -n-hexyl- | O | 3,4-difluoro |
| 21 | phenyl | -n-hexyl- | O | 3-trifluoromethyl |
| 22 | phenyl | -n-hexyl- | O | 4-trifluoromethyl |
| 24 | phenyl | -n-hexyl- | O | 4-dimethylamino |
| 25 | phenyl | -n-hexyl- | O | 4-methyl |
| 26 | phenyl | -n-hexyl- | O | 3,5-difluoro |
| 32 | 3-methoxy-phenyl | -n-hexyl- | O | 4-methyl |
| 33 | phenyl | -n-pentyl- | O | a = 0 |
| 35 | phenyl | -n-pentyl- | O | 4-methyl |
| 37 | 4-biphenyl | -n-pentyl- | O | 4-methyl |
| 39 | 4-fluoro-phenyl | -n-pentyl- | O | 4-methyl |
| 40 | 3-methoxy-phenyl | —CC—(CH$_2$)$_3$— | O | a = 0 |
| 41 | 4-methoxy-phenyl | —CC—(CH$_2$)$_3$— | O | a = 0 |
| 42 | pyrid-4-yl | -n-hexyl- | O | a = 0 |
| 43 | phenyl | —CC—(CH$_2$)$_4$— | O | a = 0 |
| 44 | 4-cyano-phenyl | -n-hexyl- | O | a = 0 |
| 45 | 4-cyano-phenyl | —CC—(CH$_2$)$_4$— | O | a = 0 |
| 46 | phenyl | —O-n-pentyl- | O | a = 0 |
| 47 | phenyl | —O-n-pentyl- | O | 4-methyl |
| 49 | 3-trifluoromethoxy-phenyl | -n-hexyl- | O | a = 0 |
| 50 | 2-chloro-quinolin-6-yl | -n-hexyl- | O | a = 0 |
| 51 | 2-fluoro-phenyl | -n-hexyl- | O | a = 0 |
| 53 | 3-fluoro-phenyl | —O-n-pentyl- | O | a = 0 |
| 63 | 3-methoxy-phenyl | —O-n-pentyl- | O | a = 0 |
| 74 | phenyl | -n-hexyl- | S | a = 0 |
| 108 | 3,5-difluoro-phenyl | —O-n-pentyl- | S | a = 0 |
| 148 | pyrimidin-2-yl | —NH-n-pentyl- | O | a = 0 |
| 149 | phenyl | -n-hexyl- | O | 4-(dimethylamino-ethylamino-carbonyl) |
| 171 | 6-fluoro-pyrid-2-yl | —NH-n-pentyl- | O | a = 0 |

TABLE 2

Representative Compounds of Formula (I)

| ID No | R¹ | L¹ | X | —L²—R⁵ |
|---|---|---|---|---|
| 52 | phenyl | —O-n-pentyl- | O | 4-phenoxy |
| 55 | 3-fluoro-phenyl | —O-n-pentyl- | O | 4-phenoxy |
| 56 | 3-fluoro-phenyl | —O-n-pentyl- | O | 3-phenoxy |
| 57 | 3-fluoro-phenyl | —O-n-pentyl- | O | 4-(4-chloro-phenoxy) |
| 58 | phenyl | -n-hexyl- | O | 3-phenoxy |
| 59 | phenyl | -n-hexyl- | O | 4-(4-chloro-phenoxy) |
| 60 | phenyl | —O-n-pentyl- | O | 3-phenoxy |
| 64 | 3-methoxy-phenyl | —O-n-pentyl- | O | 3-phenoxy |
| 65 | 3-methoxy-phenyl | —O-n-pentyl- | O | 4-phenoxy |
| 66 | phenyl | -n-hexyl- | O | 4-(3-chloro-phenoxy) |
| 67 | 3-fluoro-phenyl | —O-n-pentyl- | O | 4-(3-chloro-phenoxy) |
| 68 | phenyl | -n-hexyl- | O | 4-benzyloxy |
| 69 | 3-fluoro-phenyl | —O-n-pentyl- | O | 4-benzyloxy |
| 75 | phenyl | -n-hexyl- | O | 4-(N-methyl-N-(4-bromophenyl)-amino) |
| 76 | phenyl | -n-hexyl- | O | 4-(3-chloro-benzyloxy) |
| 77 | phenyl | -n-hexyl- | O | 4-(4-chloro-benzyloxy) |
| 78 | phenyl | -n-hexyl- | O | 4-(1-methyl-imidazol-2-yl-methoxy) |
| 80 | phenyl | -n-hexyl- | O | 4-(4-fluoro-benzyloxy) |
| 81 | phenyl | -n-hexyl- | O | 4-(4-methoxy-benzyloxy) |
| 82 | phenyl | -n-hexyl- | O | 4-(pyrid-3-yl-methoxy) |
| 83 | phenyl | -n-hexyl- | O | 4-(3-methoxycarbonyl-benzyloxy) |
| 84 | phenyl | -n-hexyl- | O | 4-(3-fluoro-benzyloxy) |
| 85 | phenyl | -n-hexyl- | O | 4-(2-fluoro-benzyloxy) |
| 86 | phenyl | -n-hexyl- | O | 4-(pyrid-4-yl-methoxy) |
| 87 | phenyl | -n-hexyl- | O | 4-(pyrimidin-2-yl-oxy) |
| 88 | phenyl | -n-hexyl- | O | 4-(pyrid-2-yl-methoxy) |
| 89 | phenyl | -n-hexyl- | O | 4-(quinolin-2-yl-methoxy) |
| 90 | phenyl | -n-hexyl- | O | 4-(3,5-difluoro-benzyloxy) |
| 91 | phenyl | -n-hexyl- | O | 4-(5-methoxycarbonyl-fur-2-yl-methoxy) |
| 92 | 2,4-difluoro-phenyl | —O-n-pentyl- | O | 4-phenoxy |
| 93 | 2,6-difluoro-phenyl | —O-n-pentyl- | O | 4-phenoxy |
| 94 | 2,5-difluoro-phenyl | —O-n-pentyl- | O | 4-benzyloxy |
| 95 | 3,5-difluoro-phenyl | —O-n-pentyl- | O | 4-phenoxy |
| 96 | 3-chloro-phenyl | —O-n-pentyl- | O | 4-benzyloxy |
| 97 | 3-chloro-phenyl | —O-n-pentyl- | O | 4-phenoxy |
| 98 | 2,5-difluoro-phenyl | —O-n-pentyl- | O | 4-phenoxy |
| 99 | 2,4-difluoro-phenyl | —O-n-pentyl- | O | 4-benzyloxy |
| 100 | 3,5-difluoro-phenyl | —O-n-pentyl- | O | 4-benzyloxy |
| 101 | 2,6-difluoro-phenyl | —O-n-pentyl- | O | 4-benzyloxy |
| 102 | 2,3-difluoro-phenyl | —O-n-pentyl- | O | 4-phenoxy |
| 103 | 2,3-difluoro-phenyl | —O-n-pentyl- | O | 4-benzyloxy |
| 104 | phenyl | -n-hexyl- | O | 4-(1H-benzo[d][1,2,3]triazol-1-yl-methoxy) |
| 105 | phenyl | -n-hexyl- | O | 4-(phenylethoxy) |
| 106 | phenyl | -n-hexyl- | O | 4-(4-fluoro-phenoxy) |
| 107 | phenyl | -n-hexyl- | O | 4-(pyrimidin-4-yl-methoxy) |
| 109 | phenyl | -n-hexyl- | O | 4-(N-methyl-N-benzyl-amino) |
| 110 | phenyl | -n-hexyl- | O | 4-(N-methyl-N-(3,4-difluoro-benzyl)-amino) |
| 111 | phenyl | -n-hexyl- | O | 4-(N-methyl-N-(pyrid-2-yl-methyl)-amino) |
| 115 | phenyl | -n-hexyl- | O | 4-(N-benzyl-N-(t-butoxycarbonyl)-amino) |
| 116 | phenyl | -n-hexyl- | O | 4-(N-benzylamino) |
| 117 | phenyl | -n-hexyl- | O | 4-(3-cyano-benzyloxy) |
| 118 | phenyl | -n-hexyl- | O | 4-(N-(3,4-difluoro-benzyl)-amino) |
| 119 | 2-fluoro-pyrid-3-yl | -n-hexyl- | O | 4-phenoxy |
| 120 | pyrimidin-5-yl | -n-hexyl- | O | 4-phenoxy |
| 121 | phenyl | -n-hexyl- | O | 4-(6-fluoro-pyrid-2-yl-methoxy) |
| 123 | phenyl | -n-hexyl- | O | 4-(N-t-butoxycarbonyl-N-(pyrid-3-yl-methyl)-amino) |
| 124 | phenyl | -n-hexyl- | O | 4-(N-(pyrid-3-yl-methyl)-amino) |
| 125 | phenyl | -n-hexyl- | O | 4-(3-t-butoxycarbonyl-benzyloxy) |
| 126 | phenyl | -n-hexyl- | O | 4-(3-carboxy-benzyloxy) |
| 127 | 6-fluoro-pyrid-3-yl | -n-hexyl- | O | 4-phenoxy |
| 128 | phenyl | -n-hexyl- | S | 4-(3-fluoro-benzyloxy) |
| 129 | phenyl | -n-hexyl- | S | 4-(benzyloxy) |
| 130 | phenyl | -n-hexyl- | S | 4-phenoxy |
| 133 | 3,5-difluoro-phenyl | —O-n-pentyl- | S | 4-phenoxy |
| 134 | 3-chloro-phenyl | —O-n-pentyl- | S | 4-phenoxy |
| 136 | 6-trifluoro-methyl-pyrid-3-yl | -n-hexyl- | O | 4-phenoxy |
| 137 | phenyl | -n-hexyl- | S | 4-(3-methoxycarbonyl-benzyloxy) |
| 138 | phenyl | -n-hexyl- | S | 4-(pyrid-3-yl-methoxy) |
| 139 | phenyl | -n-hexyl- | S | 4-(pyrid-2-yl-methoxy) |
| 140 | phenyl | -n-hexyl- | S | 4-(pyrid-4-yl-methoxy) |
| 141 | phenyl | -n-hexyl- | S | 4-(5-methoxycarbonyl-fur-2-yl-methoxy) |
| 142 | 5-aminocarbonyl-pyrid-3-yl | -n-hexyl- | O | 4-phenoxy |
| 143 | phenyl | —CH=CH—(CH₂)₄— | O | 4-phenoxy |
| 144 | phenyl | -n-hexyl- | S | 4-(3-cyano-benzyloxy) |
| 145 | phenyl | -n-hexyl- | S | 4-(2-fluoro-benzyloxy) |
| 146 | phenyl | -n-hexyl- | S | 4-(3,5-difluoro-benzyloxy) |
| 147 | phenyl | -n-hexyl- | S | 4-(2,6-dichloro-pyrid-4-yl-methoxy) |
| 150 | phenyl | -n-hexyl- | S | 4-(3-dimethylamino-carbonyl-benzyloxy) |
| 151 | phenyl | -n-hexyl- | S | 4-(6-fluoro-pyrid-2-yl-methoxy) |

TABLE 2-continued

Representative Compounds of Formula (I)

| ID No | R¹ | L¹ | X | —L²—R⁵ |
|---|---|---|---|---|
| 152 | phenyl | -n-hexyl- | S | 4-(2-fluoro-pyrid-4-yl-methoxy) |
| 154 | 4-methyl-thiazol-5-yl | -n-hexyl- | S | 4-(3-fluoro-benzyloxy) |
| 156 | phenyl | -n-hexyl- | S | 4-(pyrid-4-yl-N-oxide)-methoxy- |
| 157 | 6-(methyl-carbonyl-amino)-pyrid-3-yl | -n-hexyl- | S | 4-(3-fluoro-benzyloxy) |
| 159 | 6-fluoro-pyrid-3-yl | -n-hexyl- | S | 4-(pyrid-4-yl-methoxy) |
| 161 | phenyl | -n-hexyl- | S | 4-(3-fluoro-pyrid-4-yl-methoxy) |
| 162 | phenyl | -n-hexyl- | S | 4-(6-bromo-pyrid-2-yl-methoxy) |
| 163 | phenyl | -n-hexyl- | S | 4-(6-cyano-pyrid-2-yl-methoxy) |
| 164 | phenyl | -n-hexyl- | S | 4-(6-chloro-pyrid-2-yl-methoxy) |
| 165 | 6-fluoro-pyrid-3-yl | -n-hexyl- | S | 4-(3-fluoro-benzyloxy) |
| 166 | 4-methyl-thiazol-5-yl | -n-hexyl- | S | 4-(pyrid-4-yl-methoxy) |
| 167 | 6-fluoro-pyrid-3-yl | -n-hexyl- | S | 4-(pyrid-2-yl-methoxy) |
| 168 | 6-fluoro-pyrid-3-yl | -n-hexyl- | S | 4-(2-fluoro-pyrid-4-yl-methoxy) |
| 169 | 6-fluoro-pyrid-3-yl | -n-hexyl- | S | 4-(2-chloro-pyrid-4-yl-methoxy) |
| 170 | 6-fluoro-pyrid-3-yl | -n-hexyl- | S | 4-(3-methoxycarbonyl-benzyloxy) |
| 172 | phenyl | -n-hexyl- | O | 4-(benzyl-sulfonyl) |
| 173 | phenyl | -n-hexyl- | S | 4-(2-chloro-pyrid-4-yl-methoxy) |
| 174 | phenyl | -n-hexyl- | S | 4-(2-methyl-pyrid-4-yl-methoxy) |
| 175 | phenyl | -n-hexyl- | S | 4-(5-fluoro-pyrid-3-yl-methoxy) |
| 176 | pyrimid-2-yl | —NH-n-pentyl- | O | 4-(benzyloxy) |
| 179 | phenyl | -n-hexyl- | O | 4-phenoxy |

TABLE 3

Representative Compounds of Formula (I)

| ID No | R¹ | L¹ | A |
|---|---|---|---|
| 7 | phenyl | -n-hexyl- | benzo[d][1,3]dioxol-5-yl |
| 19 | phenyl | -n-hexyl- | 6-(2,3-dihydropyrrolo[2,1-b]quinazolin-9-one) |
| 27 | phenyl | -n-hexyl- | naphthy-2-yl |
| 28 | 3-fluoro-phenyl | -n-hexyl- | naphthy-2-yl |
| 30 | 4-fluoro-phenyl | -n-hexyl- | naphthy-2-yl |
| 31 | 3-methoxy-phenyl | -n-hexyl- | naphthy-2-yl |

TABLE 3-continued

Representative Compounds of Formula (I)

| ID No | R¹ | L¹ | A |
|---|---|---|---|
| 34 | phenyl | -n-pentyl- | naphthy-2-yl |
| 36 | 4-biphenyl | -n-pentyl- | naphthy-2-yl |
| 38 | 4-fluoro-phenyl | -n-pentyl- | naphthy-2-yl |
| 48 | phenyl | —O-n-pentyl- | naphthy-2-yl |
| 54 | 3-fluoro-phenyl | —O-n-pentyl- | naphthy-2-yl |
| 61 | phenyl | -n-hexyl- | dibenzo[b,e][1,4]dioxin-2-yl |
| 62 | 3-fluoro-phenyl | —O-n-pentyl- | dibenzo[b,e][1,4]dioxin-2-yl |
| 177 | phenyl | -n-hexyl- | 3-pyridyl |
| 178 | phenyl | -n-hexyl- | 4-pyridyl |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{1-4}$" when used with alkyl means a carbon chain composition of 1-4 carbon atoms. One skilled in the art will recognize that the term "—($C_{1-4}$alkyl)-" shall denote any $C_{1-4}$alkyl carbon chain as herein defined, wherein said $C_{1-4}$alkyl chain is divalent and is further bound through two points of attachment, preferably through two terminal carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{1-4}$" when used with alkoxy means an oxygen ether radical of the above described carbon chain alkyl group of 1-4 carbon atoms.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents. With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

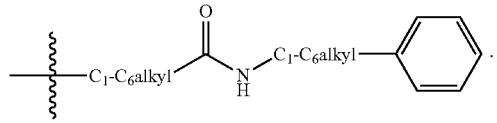

Abbreviations used in the specification, particularly the Schemes and Examples, are as follows:

| | |
|---|---|
| BOC or Boc = | tert-Butoxycarbonyl (i.e. —C(O)—O-(tert-butyl)) |
| BOC$_2$O = | Boc Anhydride (i.e. (CH$_3$)$_3$CO—C(O)—O—C(O)—OC(CH$_3$)$_3$) |
| CBz = | Carboxybenzyl (i.e. —C(O)O—CH$_2$-phenyl) |
| DCC = | Dcyclohexylcarbodiimide |
| DCM = | Dichloromethane |
| Dess-Martin or Dess-Martin Periodinane = | 1,1,1-Triacetoxy-1,1-dihydro-1,2-benziodoxol-3(1H)-one |
| DIPEA or DIEA = | Diisopropylethylamine |
| DMF = | N,N-Dimethylformamide |
| DMSO = | Dimethylsulfoxide |
| EDC or EDAC = | 1-Ethyl-3-(3-dimethylaminopropyl)carbodiimide |
| EL = | Endothelial Lipase |
| EtOAc = | Ethyl acetate |
| EtOH = | Ethanol |
| HATU = | O-(7-Azabenzotriazol-1-yl)-N,N,N'',N''-Tetramethyl Uronium Hexafluorophosphate |
| HDL = | High Density Lipoprotein |
| HEPES = | 4-(2-Hydroxyethyl)-1-Piperizine Ethane Sulfonic Acid |
| HOBT or HOBt = | 1-Hydroxybenzotriazole |
| HPLC = | High Performance Liquid Chromatography |
| LDL = | Low Density Lipoprotein |
| MeCN = | Acetonitrile |
| MeOH = | Methanol |
| Mesyl = | Methylsulfonyl |
| MOM = | Methoxymethyl Ether |
| PCC = | Pyridinium Chlorochromate |
| Pd/C = | Palladium on Carbon Catalyst |
| Pd$_2$(OAc)$_2$ = | Palladium(II)acetate |
| Pt/C = | Platinum on Carbon Catalyst |
| t-BOC or Boc = | Tert-Butoxycarbonyl |
| TEA = | Triethylamine |
| TFA = | Trifluoroacetic acid |
| THF = | Tetrahydrofuran |
| THP = | Tetrahydroipyranyl |
| TMS = | Trimethylsilyl |
| Tosyl = | p-Toluenesulfonyl |

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles - Smoles)/(Rmoles + Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee = ([\alpha\text{-obs}]/[\alpha\text{-max}]) \times 100.$$

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1.

Scheme 1

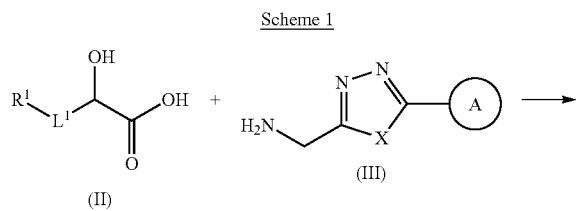

(II)    (III)

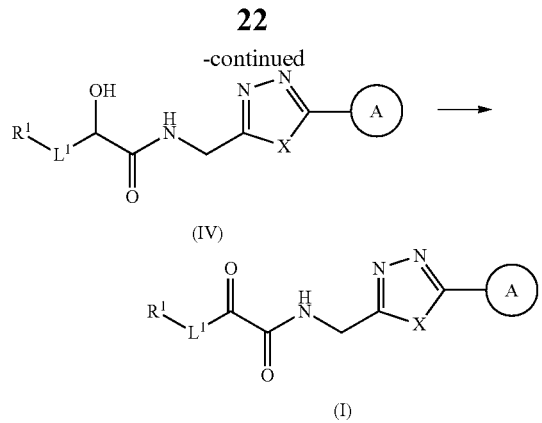

Accordingly, a suitably substituted compound of formula (II) is reacted with a suitably substituted compound of formula (III); in the presence of a suitably selected coupling agent such as HOBt/EDC, HOBt/DCC, HATU, and the like; in the presence of a suitably selected organic base such as TEA, DIPEA, pyridine, and the like; in a suitably selected organic solvent such as DMF, acetonitrile, and the like; to yield the corresponding compound of formula (IV).

The compound of formula (IV) is reacted with a suitably selected oxidizing agent such as Dess-Martin reagent, PCC, and the like; in the presence of a suitably selected solvent such as DCM, chloroform, and the like; to yield the corresponding compound of formula (I).

Compound of formula (II) may be prepared according to the process outlined in Scheme 2, below.

Scheme 2

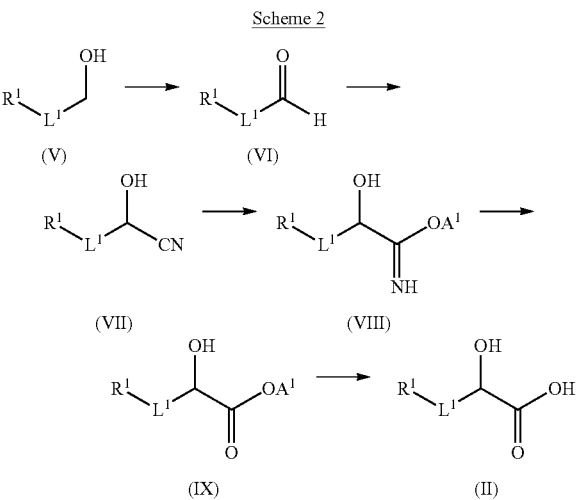

Accordingly, a suitably substituted compound of formula (V), a known compound or compound prepared by known methods, is reacted with a suitably selected oxidizing agent such as Dess-Martin reagent, PCC, and the like; in a suitably selected organic solvent such as DCM, chloroform, and the like; to yield the corresponding compound of formula (VI).

The compound of formula (VI) is reacted with a suitably selected cyanating agent such as KCN, and the like; in a suitably selected solvent mixture such as water/ethyl acetate, water, 1,4-dioxane, and the like; to yield the corresponding compound of formula (VII).

The compound of formula (VII) is reacted with a suitably selected acid such as HCl, and the like; in a suitably selected alcohol of the formula $A^1OH$, wherein $A^1$ is methyl, ethyl, and the like, preferably methyl; to yield the corresponding compound of formula (VIII).

The compound of formula (VIII) is reacted with water; in the presence of a suitably selected solvent such as ethyl acetate, and the like; to yield the corresponding compound of formula (IX).

The compound of formula (IX) is reacted with a suitably selected base such as LiOH, KOH, and the like; in a suitable solvent system such as 1,4-dioxane/water, and the like; to yield the corresponding compound of formula (II).

Compounds of formula (II) wherein $L^1$ is —O-(n-pentyl)- may alternatively be prepared according to the process outlined in Scheme 3, below.

Scheme 3

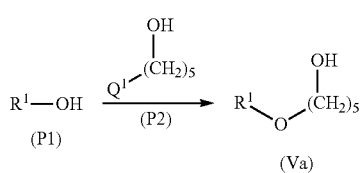

Accordingly, a suitably substituted compound of formula (P1), a known compound or compound prepared by known methods, is reacted with a suitably substituted compound of formula (P2), wherein $Q^1$ is a suitably selected leavin group such as Br, I, and the like, preferably Br, a known compound or compound prepared by known methods; in the presence of a suitably selected aqueous inorganic base such as NaOH, KOH, and the like; in water,; to yield the corresponding compound of formula (Va), a compound of formula (V) wherein $L^1$ is —O-(n-pentyl)-. Said compound of formula (Va) is then substituted for the compound of formula (V) and reacted as described in Scheme 2 above, to yield the corresponding compound of formula (IIa)

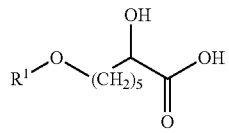

a compound of formula (II) wherein $L^1$ is —O-(n-pentyl)-.

Compounds of formula (III) may be prepared according to the process outlined in Scheme 4, below.

Scheme 4

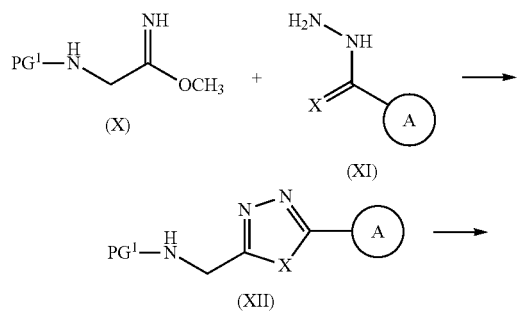

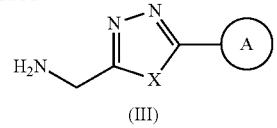

Accordingly, a suitably substituted compound of formula (X), wherein $PG^1$ is a suitably selected nitrogen protecting group such as CBz, and the like, a known compound or compound prepared by known methods, is reacted with a suitably selected compound of formula (XI), a known compound or compound prepared by known methods; in a suitably selected organic solvent such as methanol, ethanol, and the like; preferably at a temperature in the range of from about 65° C. to about 78° C. (solvent reflux temperature), more preferably at about solvent reflux temperature; to yield the corresponding compound of formula (XII).

One skilled in the art will recognize that in the compound of formula (X), the methoxy group may alternatively be replaced with an ethoxy group (—OCH$_2$CH$_3$) and said compound reacted as described above, to yield the corresponding compound of formula (XI).

The compound of formula (XII) is de-protected, according to known methods, to yield the corresponding compound of formula (I). For example, wherein $PG^1$ is CBz, the compound of formula (XII) is de-protected by reacting with 33% HBr in acetic acid.

Compounds of formula (I) wherein $R^1$ is a hetero-atom containing aromatic ring structure (e.g. pyridyl, pyrimidinyl, thiazolyl, quinolinyl) and wherein $L^1$ is selected from the group consisting of -(n-hexyl), —NH-(n-pentyl)- and —CH═CH-(n-hexyl)-, may alternatively be prepared according to the process outlined in Scheme 5, below.

Scheme 5

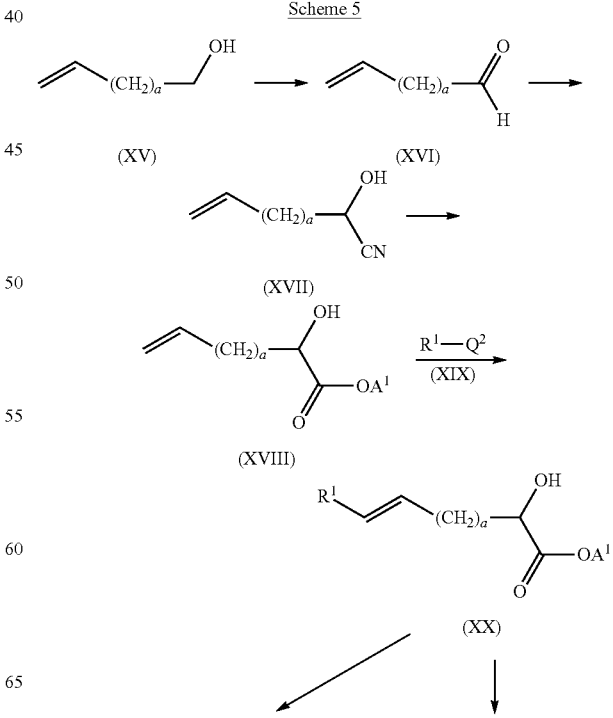

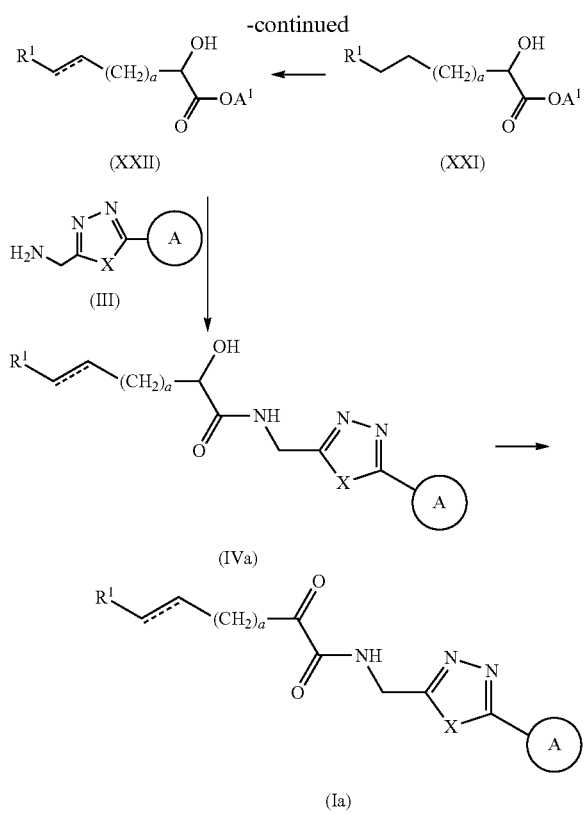

Accordingly, a suitably substituted compound of formula (XV), wherein a is an integer from 3 to 4, a known compound or compound prepared by known methods, is reacted with a suitably selected oxidizing agent such as PCC, Dess-Martin periodinane, and the like; in a suitably selected organic solvent such as $CH_2Cl_2$, $CHCl_3$, and the like; to yield the corresponding compound of formula (XVI).

The compound of formula (XVI) is reacted with a suitably selected cyanating agent such as NaCN, KCN, and the like; in a suitably selected solvent mixture such as EtOAc/water; 1,4-dioxane/water, and the like; to yield the corresponding compound of formula (XVII).

The compound of formula (XVII) is reacted with a suitably selected acid such as HCl, and the like; in a suitably selected alcohol of the formula $A^1OH$, wherein $A^1$ is methyl, ethyl, and the like, preferably methyl; and then treated with a suitably selected base such as aqueous $NaHCO_3$, and the like; to yield the corresponding compound of formula (XVIII).

The compound of formula (XVIII) is reacted with a suitably substituted compound of formula (XIX), wherein $Q^2$ a suitably selected leaving group such as Br, Cl, I, and the like, a known compound or compound prepared by known methods; in the presence of a suitably selected palladium reagent such as $Pd_2(OAc)_2$, and the like; in the presence of a suitably selected organic base such as TEA, DIPEA, and the like; in a suitably selected organic solvent such as DMF, toluene, THF, and the like; to yield the corresponding compound of formula (XX).

The compound of formula (XX) is optionally reacted with a suitably selected reducing agent such as $H_2(g)$, and the like; in the presence of a suitably selected catalyst such as Pd/C, Pt/C, and the like; in a suitably selected organic solvent such as methanol, ethanol, and the like; to yield the corresponding compound of formula (XXI).

The compound of formula (XXI) is reacted with a suitably selected base such as LiOH, NaOH, KOH, and the like; in a mixture of water and a suitably selected organic solvent such as THF, 1,4-dioxane, and the like; to yield the corresponding compound of formula (XXII).

The compound of formula (XXII) is reacted with a suitably substituted compound of formula (III); in the presence of suitably selected coupling agents such as HOBt/EDC, HOBt/DCC, and the like; in the presence of a suitably selected organic base such as TEA, DIPEA, and the like; in a suitably selected organic solvent such as DMF, acetonitrile, and the like; to yield the corresponding compound of formula (IVa).

The compound of formula (IVa) is reacted with a suitably selected oxidizing agent such as Dess-Martin reagent, PCC, and the like; in suitably selected organic solvent such as DCM, chloroform, and the like; to yield the corresponding compound of formula (Ia), a compound of formula (I) wherein $L^1$ is selected from the group consisting of -(n-hexyl), —NH-(n-pentyl)- and —CH=CH-(n-hexyl)-.

Compounds of formula (I) wherein $L^1$ is —NH-(n-pentyl)-, wherein

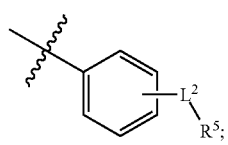

is

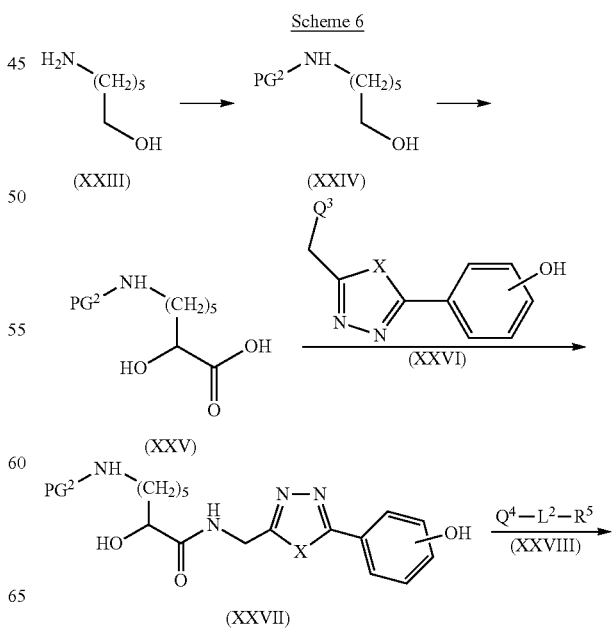

and wherein the -$L^2$-$R^5$ group is bound at the 3- or 4-position of the phenyl, may alternatively be prepared according to the process outlined in Scheme 6, below.

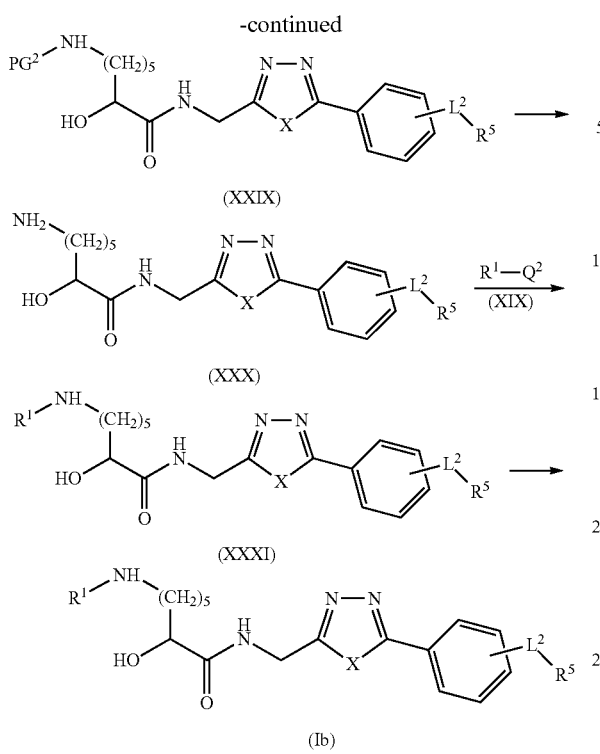

Accordingly, a suitably substituted compound of formula (XXIII), a known compound or compound prepared by known methods, protected, according to known methods, to yield the corresponding compound of formula (XXIV), wherein $PG^2$ is the corresponding nitrogen protecting group such as CBz, and the like.

The compound of formula (XXIV) is reacted according to the process outlined in Scheme 2, to yield the corresponding compound of formula (XXV). More particularly, the compound of formula (XXIV) is substituted for the compound of formula (V) in Scheme 2 and reacted as described, to yield the corresponding compound of formula (XXV).

The compound of formula (XXV) is reacted with a suitably substituted compound of formula (XXVI), wherein $Q^3$ is a suitably selected leaving group such as Br, I, and the like, preferably Br, and wherein the hydroxy group (—OH) is bound at the 3- or 4-position of the phenyl (i.e. the desired position to which the -$L^2$-$R^5$ substituent group is to be bound), a known compound or compound prepared by known methods; in the presence of a suitably selected coupling agent such as HOBT/EDC, HOBt/DCC, HATU, and the like; in the presence of a suitably selected organic base such as TEA, DIPEA, pyridine, and the like; in a suitably selected organic solvent such as DMF, acetonitrile, and the like; to yield the corresponding compound of formula (XXVII).

The compound of formula (XXVII) is reacted with a suitably selected compound of formula (XXVIII), wherein $Q^4$ is a suitably selected leaving group such as Br, I, and the like, preferably Br, a known compound or compound prepared by known methods; in the presence of a suitably selected inorganic base such as $K_2CO_3$, $Na_2CO_3$, and the like; in a suitably selected organic solvent such as DMF, 1,4-dioxane, acetonitrile, and the like; to yield the corresponding compound of formula (XXIX).

The compound of formula (XXIX) is de-protected according to known methods, to yield the corresponding compound of formula (XXX). For example, wherein $PG^2$ is Cbz, the compound of formula (XXIX) is de-protected by reacting with 33% HBr in acetic acid.

The compound of formula (XXX) is reacted with a suitably substituted compound of formula (XIX), wherein $Q^2$ a suitably selected leaving group such as Br, Cl, I, and the like, a known compound or compound prepared by known methods; in the presence of a suitably selected palladium reagent such as $Pd_2(OAc)_2$, and the like; in the presence of a suitably selected organic base such as TEA, DIPEA, and the like; in a suitably selected organic solvent such as DMF, toluene, THF, and the like; to yield the corresponding compound of formula (XXXI).

The compound of formula (XXXI) is reacted with a suitably selected oxidizing agent such as Dess-Martin reagent, PCC, and the like; in a suitably selected organic solvent such as DCM, chloroform, and the like; to yield the corresponding compound of formula (Ib), a compound of formula (I) wherein $L^1$ is —NH-(n-pentyl)-, and wherein wherein (A)

is

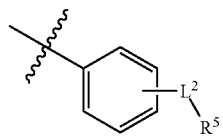

as herein defined.

One skilled in the art will further recognize that the various reaction steps (one or more) outlined in Schemes 1 through 6 above may be applied in other combination(s) and/or order(s) to produce alternately schemes for the preparation of the compounds of formula (I) of the present invention. Further one skilled in the art would readily recognize how such reaction step(s), combination(s) and/or order(s) should be arranged to yield the desired compounds of formula (I) of the present invention.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1000 mg or any amount range therein, and may be given at a dosage of from about 0.01 to about 15 mg/kg/day, or any amount range therein, preferably from about 0.1 to about 10 mg/kg/day, or any amount range therein, preferably from about 0.5 to about 5 mg/kg/day, or any amount range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably, between about 1.0 mg and about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

The daily dosage of the products may be varied over a wide range from about 0.01 to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 15 mg/kg of body weight per day, or any amount or range therein. Preferably, the range is from about 0.1 to about 10.0 mg/kg of body weight per day, or any amount or range therein. More preferably, from about 0.5 to about 5.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

SYNTHESIS EXAMPLE 1

2-oxo-8-phenyl-N-((5-phenyl-1,3,4-oxadiazol-2-yl)methyl)octanamide Compound #1

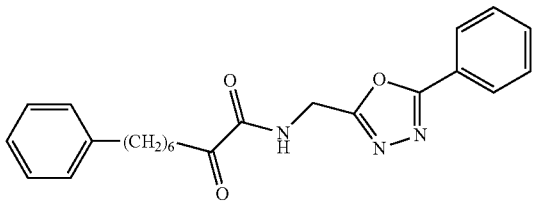

A solution of 7-phenylheptan-1-ol (5 g) in CH$_2$Cl$_2$ (25 mL) was added to a suspension of 1,1,1-tris(acetyloxy)1,1-dihydro-1,2-benziodoxol-3-(1H)-one (Dess-Martin periodinane) in CH$_2$Cl$_2$ (25 mL) dropwise with ice-bath cooling. The cooling bath was removed after addition was complete and the resulting mixture was stirred at room temperature for 3 h. After addition of a solution of Na$_2$S$_2$O$_3$ (44 g) in saturated NaHCO$_3$, (35 mL), the resulting mixture was stirred for 45 min and the layers were separated. The aqueous layer was extracted twice with CH$_2$Cl$_2$, and the combined organic phases were washed with water, dried over Na$_2$SO$_4$ and concentrated to yield 7-phenylheptanal as an oil, which was used in the next step without further purification.

A two-phase mixture of ethyl acetate (30 mL) and water (35 mL) containing 7-phenylheptanal (5.2 g) and KCN (7.1 g) was stirred vigorously at room temperature for 24 h. The layers were separated and the aqueous phase was washed with water, dried (Na$_2$SO$_4$) and concentrated to yield 2-hydroxy-8-phenyloctanenitrile as an oil.

A solution of 2-hydroxy-8-phenyloctanenitrile (5 g) in methanol (50 mL) was cooled to −78° C. and a stream of HCl (g) was introduced for 4 min. The mixture was stored at −10° C. for 15 h, then concentrated to yield methyl 2-hydroxy-8-phenyloctanimidate. (MH+=286).

A two-phase solution of the 2-hydroxy-8-phenyloctanimidate, ethyl acetate (50 mL), and water (50 mL) was stirred overnight. The layers were separated and the organic phase was dried (Na$_2$SO$_4$), filtered and concentrated to yield methyl 2-hydroxy-8-phenyloctanoate as an oil. The oil was dissolved in 9:1 dioxane-water (50 mL) containing LiOH (1.7 g). After 2 h of stirring, the mixture was acidified with 2N HCL to pH~3. The resulting mixture was extracted twice with EtOAc and the combined organic phases were washed with brine, dried (Na$_2$SO$_4$), filtered and concentrated to yield 2-hydroxy-8-phenyloctanoic acid as a solid.

To a solution of 2-hydroxy-8-phenyloctanoic acid (458 mg, 1.94 mmol), 5-phenyl-1,3,4-oxadiazol-2-yl methanamine oxalate (514 mg, 1.94 mmol), HOBt (314 mg, 2.3 mmol) and diisopropylethyl amine (501 mg, 3.9 mmol) in DMF (15 mL) was added 1-ethyl-3(3-dimethylaminopropyl) carbodiimide hydrochloride (446 mg, 2.3 mmol). The suspension was stirred for 48 h then filtered. The filtrate was diluted with EtOAc and washed sequentially with water, saturated NaHCO$_3$, and brine. The organic phase was dried (Na$_2$SO$_4$) and filtered and the residue triturated with EtOAc to yield 2-hydroxy-8-phenyl-N-((5-phenyl-1,3,4-oxadiazol-2-yl)methyl)octanamide (MH+=394).

A solution of 2-hydroxy-8-phenyl-N-((5-phenyl-1,3,4-oxadiazol-2-yl)methyl)octanamide (362 mg) in CH$_2$Cl$_2$ (4 mL) was added to a solution of the Dess-Martin periodinane (1.5 g) in CH$_2$Cl$_2$ (4 mL). After 2 h, a solution of Na$_2$S$_2$O$_3$ (872 g) in saturated NaHCO$_3$ was added to the mixture, which was stirred for 1 h. The layers were separated and the organic phase was dried over Na$_2$SO$_4$, filtered and concentrated. Purification of the residue by chromatography (silica gel; EtOAc-heptane) yielded the title compound as a solid.

MS m/z 392; $^1$H NMR (400 MHz, CDCl$_3$) δ: 8.03-7.47 (m, 11H), 4.81 (m, 2H), 2.95 (m 2H), 2.55-2.65 (m, 2H), 1.63-1.36 (m, 8H).

SYNTHESIS EXAMPLE 2

N-((5-(4-((3-fluorobenzyl)oxy)phenyl)-1,3,4-thiadiazol-2-yl)methyl)-2-oxo-8-phenyloctanamide Compound 128

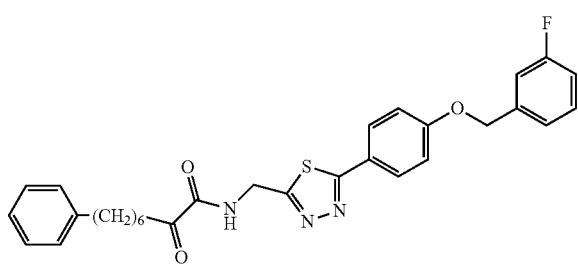

Di-t-butyl dicarbonate (10.8 g, 49.5 mmol) was added to a solution of 4-(benzyloxy)benzohydrazide (10 g, 41.3 mmol) in dichloromethane (206 mL) at 0° C. The resulting mixture was stirred for 2 d at room temperature, then concentrated and the residue was triturated with diethyl ether to yield tert-butyl 2-(4-(benzyloxy)benzoyl)hydrazinecarboxylate. A mixture of tert-butyl 2-(4-(benzyloxy)benzoyl)hydrazinecarboxylate (13.7 g, 40 mmol) and Lawesson's reagent (8.1 g, 20.0 mmol) in THF (200 mL) THF was stirred for 2 d. Solvent was removed under vacuum and the residue was chromatographed (silica gel, heptane-ethyl acetate) to yield tert-butyl 2-(4-(benzyloxy)phenylcarbonothioyl)hydrazinecarboxylate. A solution of tert-butyl 2-(4-(benzyloxy)phenylcarbonothioyl)hydrazinecarboxylate(12 g) in 1,4-dioxane (34 mL) and 4.0 N HCl (34 mL) in 1,4-dioxane was stirred for 5 h. The resulting solid was collected and washed with diethyl ether to yield 4-(benzyloxy)benzothiohydrazide.

To a solution of benzyl (2-amino-2-oxoethyl)carbamate (8.5 g, 40.8 mmol) in CH$_2$Cl$_2$ (204 mL) was added trimethyloxonium tetrafluoroborate (6.0 g, 40.8 mmol) in one portion. The resulting mixture was stirred for 24 h, then acidified to pH~3 with 1N ethereal HCl. The resulting mixture was concentrated under reduced pressure to yield methyl 2-(((benzyloxy)carbonyl)amino)acetimidate. A solution of methyl 2-(((benzyloxy)carbonyl)amino)acetimidate (9.3 g, 36 mmol), 4-(benzyloxy)benzothiohydrazide (8.0 g, 24 mmol) and diisopropylethylamine (4.2 mL, 24 mmol) in methanol (480 mL) was refluxed for 12 h. The resulting mixture was cooled to room temperature, at which point benzyl ((5-(4-(benzyloxy)phenyl)-1,3,4-thiadiazol-2-yl)methyl)carbamate precipitated and was collected (MS m/z=432 MH+).

A solution of benzyl((5-(4-(benzyloxy)phenyl)-1,3,4-thiadiazol-2-yl)methyl)carbamate (7.4 g, 17.1 mmol) in 33% HBr in acetic acid (100 mL) and was stirred for 2 h. The resulting mixture was diluted with diethyl ether and the precipitate was collected and washed with diethyl ether to yield 4-(5-(aminomethyl)-1,3,4-thiadiazol-2-yl)phenol (MS m/z=408 MH+).

A solution of 4-(5-(aminomethyl)-1,3,4-thiadiazol-2-yl) phenol (1 g, 3.5 mmol) in methanol (9 mL) containing NaHCO$_3$ (1.2 g, 13.9 mmol) and di-t-butyldicarbonate (Boc$_2$O; 1.5 g, 7.0 mmol) was stirred for 5 h. The resulting mixture was filtered and the filtrate concentrated. The residue was dissolved in CH$_2$Cl$_2$ (48 mL) and treated with 0.5 M NaOCH$_3$ in methanol (8.3 mL). After stirring at room temperature for 1 h, the volatiles were removed under vacuum to yield tert-butyl ((5-(4-hydroxyphenyl)-1,3,4-thiadiazol-2-yl) methyl)carbamate. To a solution of tert-butyl((5-(4-hydroxyphenyl)-1,3,4-thiadiazol-2-yl)methyl)carbamate (1.01 g, 2.89 mmol), dimethylformamide (16 mL) and potassium carbonate (1.36 g, 9.86 mmol) was added 3-fluorobenzylbromide (0.61 mL, 4.93 mmol), and the mixture was stirred at room temperature overnight. After 24 h, the resulting mixture was filtered and the filtrate was concentrated. The residue was purified by chromatography (silica gel, heptane:EtOAc) to yield tert-butyl((5-(4-((3-fluorobenzyl)oxy)phenyl)-1,3,4-thiadiazol-2-yl)methyl)carbamate. $^1$H NMR (400 MHz, CDCl$_3$) δ 7.87-7.92 (m, 2H), 7.33-7.42 (m, 1H), 7.14-7.23 (m, 2H), 7.01-7.08 (m, 3H), 5.13 (s, 2H), 4.68-4.77 (m, 2H), and 1.48 (s, 9H); MS (ES$^+$) 416 (M+1).

A solution of tert-butyl ((5-(4-((3-fluorobenzyl)oxy)phenyl)-1,3,4-thiadiazol-2-yl)methyl)carbamate, dioxane (16 mL), and 4N HCl in dioxane (13 ml) was stirred at room temperature for 4 h. The resulting mixture was concentrated in vacuo to yield (5-(4-((3-fluorobenzyl)oxy)phenyl)-1,3,4-thiadiazol-2-yl)methanamine, which was in the next step used directly without further purification. MS (ES$^+$) 316 (MH+).

A solution of (5-(4-((3-fluorobenzyl)oxy)phenyl)-1,3,4-thiadiazol-2-yl)methanamine (0.85 mmol), 2-hydroxy-8-phenyloctanoic acid (0.85 mmol), 1-hydroxybenzotriazole hydrate (1.0 mmol), N-(3-dimethylaminopropyl)-N'-ethylcarbodiimide hydrochloride (1.0 mmol), and DIPEA (3.4 mmol) in dimethylformamide (4 mL) was stirred at room temperature for 22 h. The resulting mixture was diluted with NaHCO$_3$ (saturated) and extracted twice with ethyl acetate. The organic phases were combined, washed with brine, dried (Na$_2$SO$_4$) and concentrated. The residue was purified by silica gel chromatography (MeOH—CH$_2$Cl$_2$) to yield N-((5-(4-((3-fluorobenzyl)oxy)phenyl)-1,3,4-thiadiazol-2-yl)methyl)-2-hydroxy-8-phenyloctanamide. A solution of N-((5-(4-((3-fluorobenzyl)oxy)phenyl)-1,3,4-thiadiazol-2-yl) methyl)-2-hydroxy-8-phenyloctanamide (0.22 mmol) in CH$_2$Cl$_2$ (5 mL) was treated with the Dess-Martin periodinane (0.34 mmol) and stirred overnight. The resulting mixture was quenched with a solution of sodium thiosulfate dissolved in saturated aqueous NaHCO$_3$, and the mixture was extracted twice with ethyl acetate. The combined organic extracts were washed with brine, dried (Na$_2$SO$_4$) and concentrated. The residue was purified by chromatography (silica gel, heptane-ethyl acetate) to yield the title compound.

$^1$H NMR (400 MHz, CDCl$_3$) δ 7.88 7.07 (m, 13H), 5.12 (m, 2H), 4.90 (m 2H), 2.57-2.62 (m, 4H), 1.56-1.36 (m, 8H).

SYNTHESIS EXAMPLE 3

N-((5-(4-((3-fluorobenzyl)oxy)phenyl)-1,3,4-thiadiazol-2-yl)methyl)-8-(4-methylthiazol-5-yl)-2-oxooctanamide Compound #154

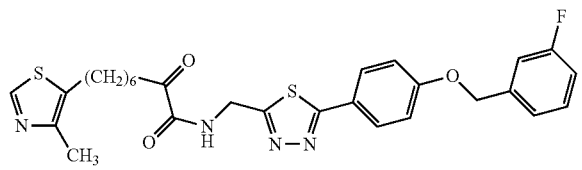

Pyridinium chlorochromate (19.26 g, 0.088 mol) was added to a solution of hept-6-en-1-ol (5.0 g, 0.044 mol) and dichloromethane (600 mL). The resulting mixture was stirred at room temperature for 2 h, then diluted with diethyl ether, filtered through silica gel and concentrated in vacuo below room temperature to yield hept-6-enal as an oil, which was used in the next step without further purification. To a solution of hept-6-enal (4.9 g, 0.044 mol) in ethyl acetate (36 mL) was added a solution of sodium cyanide (6.4 g, 0.13 mol) in water (36 mL) and the resulting mixture was stirred at room temperature for 24 h. The layers were separated and the aqueous layer was extracted 2 times with ethyl acetate. The combined organic layers were dried (MgSO$_4$) filtered and concentrated in vacuo to yield 2-hydroxyoct-7-enenitrile as a tan oil, which was used in the next step without further purification. A stream of HCl(g) was introduced into a solution of 2-hydroxyoct-7-enenitrile (6.0 g, 0.043 mmol) and methanol (130 mL) at −78° C. for 5 min. The resulting mixture was stored at −10° C. for 18 h, then concentrated in vacuo. The residue was diluted with ethyl acetate (106 mL) and water (106 mL) and the solution was stirred at room temperature overnight. The layers were separated, and the organic layer was dried with MgSO$_4$, filtered, and concentrated in vacuo to yield methyl 2-hydroxyoct-7-enoate. $^1$H NMR (400 MHz, CDCl$_3$) δ 5.48-5.82 (m, 1H), 4.89-5.08 (m, 2H), 4.31-4.52 (m, 1H), 3.79 (s, 3H), 2.78-3.12 (bs, 1H), 2.02-2.28 (m, 2H), 1.75-1.89 (m, 1H), 1.68-1.70 (m, 1H), and 1.38-1.52 (m, 4H).

A mixture of methyl 2-hydroxyoct-7-enoate (6.88 g, 0.040 mmol), dichloromethane (40 mL), 3,4-dihydro-2H-pyran (7.4 mL, 0.082 mol), and 6 drops of trifluoroacetic acid was stirred at room temperature overnight. The resulting mixture was concentrated in vacuo to yield methyl 2-(cyclohexyloxy) oct-7-enoate, which was used in the next step without further purification. A solution of methyl 2-(cyclohexyloxy)oct-7-enoate (500.0 mg, 1.95 mmol) dissolved in toluene (33 mL) containing 4-methyl-5-vinylthiazole (1.11 mL, 19.5 mmol) and Grubb's 2$^{nd}$ generation catalyst (166 mg, 0.195 mmol) was flushed with argon and heated in a sealed tube at 100° C. for 20 h. After cooling to room temperature, the solvent was removed in vacuo and the resulting residue was purified via flash silica gel chromatography (Analogix IF-280, SF25-115 g column, gradient 90:10-80:20 Heptane:EtOAc) to yield (E)-methyl 2-(cyclohexyloxy)-8-(4-methylthiazol-5-yl)oct-7-enoate. MS (ES$^+$) 354 (M+1).

To a solution of (E)-methyl 2-(cyclohexyloxy)-8-(4-methylthiazol-5-yl)oct-7-enoate (560 mg, 1.58 mmol) and ethanol (40 mL) was added 10% palladium on carbon (82 mg) and the resulting mixture was hydrogenated at 1 atm H$_2$ overnight. The resulting mixture was then filtered through CELITE and concentrated in vacuo to yield methyl 2-(cyclohexyloxy)-8-(4-methylthiazol-5-yl)octanoate (97%) which was used in the next step without further purification. A solution of methyl 2-(cyclohexyloxy)-8-(4-methylthiazol-5-yl)octanoate (563 mg, 1.58 mmol), methanol (8.6 mL), and p-toluenesulfonic acid (14.8 mg, 0.086 mmol) was stirred at room temperature for 1 h. Solvent was removed in vacuo to yield methyl 2-hydroxy-8-(4-methylthiazol-5-yl)octanoate which was used in the next step without further purification. A mixture of 2-hydroxy-8-(4-methylthiazol-5-yl)octanoic acid (590 mg, 2.17 mmol), tetrahydrofuran (21 mL), water (54 mL) and lithium hydroxide (78.1 mg, 3.26 mmol) was stirred at room temperature for 2 h. The resulting mixture was acidified with 1N HCl and concentrated in vacuo. An excess amount of acetonitrile was added to the residue and the mixture was concentrated. The process was repeated twice to yield 2-hydroxy-8-(4-methylthiazol-5-yl)octanoic acid which was used in the next step without further purification. MS (ES$^+$) 258 (M+1).

A mixture of 2-hydroxy-8-(4-methylthiazol-5-yl)octanoic acid (40.0 mg, 0.155 mmol), 1-hydroxybenzotriazole hydrate (21.0 mg, 0.155 mmol), N-(3-dimethylaminopropyl)-N'-ethylcarbodiimide hydrochloride (44.7 mg, 0.233 mmol), triethylamine (0.06 mL, 0.466 mmol) and (5-(4-((3-fluorobenzyl)oxy)phenyl)-1,3,4-thiadiazol-2-yl)methanamine (54.7 mg, 0.155 mmol) in dimethylformamide (0.78 mL) was stirred at room temperature for 22 h. The resulting mixture was concentrated and the residue was purified via silica gel chromatography (Analogix IF-280, SF25-40 g column, gradient 90:10-80:20 heptane:EtOAc) to yield N-((5-(4-((3-fluorobenzyl)oxy)phenyl)-1,3,4-thiadiazol-2-yl)methyl)-2-hydroxy-8-(4-methylthiazol-5-yl)octanamide. MS (ES$^+$) 555 (M+1).

A solution of N-((5-(4-((3-fluorobenzyl)oxy)phenyl)-1,3,4-thiadiazol-2-yl)methyl)-2-hydroxy-8-(4-methylthiazol-5-yl)octanamide (60.2 mg, 0.109 mmol) in dichloromethane (1 mL) was added dropwise to 1,1,1-tris(acetyloxy)1,1-dihydro-1,2-benziodoxol-3-(1H)-one (92.0 mg, 0.217 mmol) in dichloromethane (2.0 mL). The resulting mixture was stirred at room temperature for 2.5 h, then quenched with a solution of sodium thiosulfate in saturated aqueous sodium bicarbonate. The resulting mixture was extracted with dichloromethane, and the combined extracts were dried (MgSO$_4$) and concentrated in vacuo. The resulting residue was purified via silica gel chromatography (Analogix IF-280, SF25-40 g column, gradient 100:0-98:2 dicholormethane:methanol) to yield the title compound.

$^1$H NMR (300 MHz, CDCl$_3$) 8.56 (s, 1H), 7.81-7.98 (m, 2H), 7.32-7.41 (m, 1H), 7.13-7.21 (m, 2H), 6.98-7.07 (m, 3H), 5.13 (s, 2 H), 4.23 (s, 2H), 2.91-3.01 (m, 2H), 2.71-2.78 (m, 2H), 2.34 (s, 3H), 1.56-1.72 (m, 4H), and 1.22-1.43 (m, 4H); MS (ES$^+$) 553 (M+1).

SYNTHESIS EXAMPLE 4

Methyl 3-((4-(5-(6-(2-(6-fluoropyridin-3-yl)-2-oxoacetamido)hexyl)-1,3,4-thiadiazol-2-yl)phenoxy) methyl)benzoate Compound #170

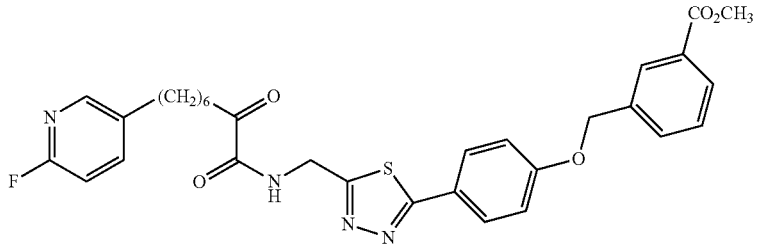

A mixture of methyl 2-hydroxyoct-7-enoate (5.0 g, 0.029 mol), 5-bromo-2-fluoropyridine (6.3 g, 0.035 mol), triethylamine (60 mL), pyridine (6.0 mL), palladium acetate (0.326 g, 0.0014 mol), and tri(o-tolyl)phosphine (1.77 g, 0.0058 mmol) in DMF (30 mL) was heated in a screw-top tube under argon at 100° C. for 3 days. After cooling to room temperature, the resulting mixture was diluted with ethyl acetate and washed sequentially with saturated aqueous ammonium chloride and brine. The organic layer was dried (MgSO$_4$) filtered, and concentrated. The resulting residue was purified by a reversed phase chromatography (Kromasil column (10 u, 100 Å C18, column length 250×50 mm, gradient 80:20-10:90 TFA-H$_2$O:MeCN). The isolated product was dissolved in ethyl acetate and washed with saturated aqueous ammonium bicarbonate. The organic layer was dried (MgSO$_4$) filtered and concentrated to yield (E)-methyl 8-(6-fluoropyridin-3-yl)-2-hydroxyoct-7-enoate. A slurry of (E)-methyl 8-(6-fluoropyridin-3-yl)-2-hydroxyoct-7-enoate (3.0 g, 0.011 mol), 10% palladium on carbon (0.5 g), and ethanol (56 mL) was hydrogenated at 20 psi H$_2$ for 24 h. The resulting mixture was filtered through CELITE and concentrated to yield methyl 8-(6-fluoropyridin-3-yl)-2-hydroxyoctanoate which was used in the next step without further purification. A mixture of methyl 8-(6-fluoropyridin-3-yl)-2-hydroxyoctanoate (3.0 g, 11.1 mmol), tetrahydrofuran (56 mL), water (139 mL) and lithium hydroxide (1.33 g, 55.7 mmol) was stirred at room temperature for 2 h. After washing with diethyl ether, the aqueous layer was acidified with 1N HCl and extracted with ethyl acetate. The organic layer was dried over MgSO$_4$ filtered and concentrated to yield 8-(6-fluoropyridin-3-yl)-2-hydroxyoctanoic acid which was used in the next step without further purification. To a solution of 8-(6-fluoropyridin-3-yl)-2-hydroxyoctanoic acid (2.0 g, 7.83 mmol), 1-hydroxybenzotriazole hydrate (1.27 g, 9.40 mmol), N-(3-dimethylaminopropyl)-N'-ethylcarbodiimide hydrochloride (1.80 g, 9.40 mmol), and dimethylformamide (20 mL) was added diisopropylethylamine (5.5 mL, 31.3 mmol) and 4-(5-(aminomethyl)-1,3,4-thiadiazol-2-yl)phenol (2.26 g, 7.83 mmol). After stirring at room temperature for 24 h, the resulting mixture was diluted with ethyl acetate and washed sequentially with saturated aqueous ammonium bicarbonate and brine. The organic extracts were dried (Na$_2$SO$_4$) and concentrated, and the resulting residue was purified by silica gel chromatography (Analogix IF-280, SF65-400 g column, gradient 100:0-80:20 dichloromethane:ethanol) to yield 8-(6-fluoropyridin-3-yl)-2-hydroxy-N-((5-(4-hydroxyphenyl)-1,3,4-thiadiazol-2-yl) methyl)octanamide. Methyl 3-(bromomethyl)benzoate (79.7 mg, 0.337 mmol) was added to a solution of 8-(6-fluoropyridin-3-yl)-2-hydroxy-N-((5-(4-hydroxyphenyl)-1,3,4-thiadiazol-2-yl)methyl)octanamide (100 mg, 0.225 mmol), cesium carbonate (220 mg, 0.675 mmol), and dimethylformamide (4.09 mL) and stirred for 20 h. The resulting mixture was diluted with ethyl acetate and washed with water. The layers were separated and the organic layer was dried (Na$_2$SO$_4$) and concentrated. Purification of the resulting residue by reversed phase chromatography on a Gilson HPLC with a Kromasil column (10 u, 100 Å C18, column length 250×50 mm, gradient 60:40-10:90 TFA-H$_2$O:MeCN) yield methyl 3-((4-(5-((8-(6-fluoropyridin-3-yl)-2-hydroxyoctanamido)methyl)-1,3,4-thiadiazol-2-yl)phenoxy)methyl) benzoate. A solution of methyl 3-((4-(5-((8-(6-fluoropyridin-3-yl)-2-hydroxyoctanamido)methyl)-1,3,4-thiadiazol-2-yl) phenoxy)methyl)benzoate (28.0 mg, 0.040 mmol) in dichloromethane (5.0 mL) was added dropwise to a mixture of 1,1,1-tris(acetyloxy)1,1-dihydro-1,2-benziodoxol-3-(1H)-one (33.6 mg, 0.079 mmol) and dichloromethane (4.0 mL). After stirring at room temperature for 2.5 h, the resulting mixture was quenched with a solution of sodium thiosulfate in saturated aqueous ammonium bicarbonate. The mixture was then extracted with dichloromethane, and the organic extract was dried (MgSO$_4$) and concentrated. Purification of the resulting residue by reversed phase chromatography on a Gilson HPLC with a Kromasil column (10 u, 100 Å C18, column length 250×50 mm, gradient 55:45-10:90 H$_2$O: MeCN) yielded the title compound.

$^1$H NMR (400 MHz, CDCl$_3$) δ 8.14 (s, 1H), 7.99-8.09 (m, 2H), 7.87-7.94 (m, 2H), 7.77-7.84 (m, 1H), 7.66-7.76 (m, 1H), 7.50-7.57 (m, 1H), 7.14-7.20 (m, 2H), 6.91-7.02 (m, 1H), 5.25 (s, 2H), 4.79-4.86 (m, 2H), 3.93 (s, 3H), 2.85-2.94 (m, 2H), 2.62-2.69 (m, 2H), 1.59-1.70 (m, 4H), 1.33-1.45 (m, 4H); MS (ES$^+$) 591 (M+1).

SYNTHESIS EXAMPLE 5

N-((5-(4-(benzyloxy)phenyl)-1,3,4-oxadiazol-2-yl) methyl)-7-(3-fluorophenoxy)-2-oxoheptanamide Compound #69

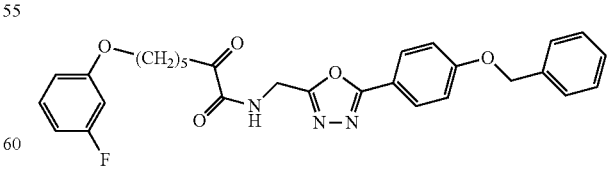

A solution of 1 M NaOH (17.8 mL) was added to a refluxing mixture of 3-fluorophenol (2 g, 17.8 mmol) and 5-bromo-1-hexanol (3.23 g, 17.8 mmol) in water (20 mL). After 3 h, the resulting mixture was cooled to room temperature and diluted with diethyl ether. The layers were separated, the organic layer was washed sequentially with 1N NaOH and water, then dried (Na$_2$SO$_4$) and concentrated to yield 6-(3-fluorophenoxy)hexan-1-ol as an oil. A solution of 6-(3-fluorophenoxy)hexan-1-ol (2.9 g, 13.67 mmol) was added dropwise to a mixture of 1,1,1-tris(acetyloxy)1,1-dihydro-1,2-benziodoxol-3-(1H)-one (7.0 g, 16.4 mmol) with ice-bath cooling. The resulting solution was stirred for 2.5 h at room temperature, then poured into a solution of sodium thiosulfate in saturated aqueous sodium bicarbonate. After 0.5 h, the layers were separated and the aqueous layer was extracted with CH$_2$Cl$_2$. The organic phase was dried (Na$_2$SO$_4$) filtered and concentrated to yield 6-(3-fluorophenoxy)hexanal. A solution of 6-(3-fluorophenoxy)hexanal (2.9 g, 13.8 mmol) in ethyl acetate (20 mL) and water (20 mL) containing NaCN (2 g, 41.4 mmol) was stirred vigorously overnight. After 20 h, the phases were separated and the aqueous layer was extracted twice with ethyl acetate. The combined ethyl acetate layers were washed with water, dried (Na$_2$SO$_4$) and concentrated to yield 7-(3-fluorophenoxy)-2-hydroxyheptanenitrile, which was dissolved in methanol (40 mL) and cooled to −78° C. The solution was saturated with HCl (g) and stored at −10° C. for 18 h. The resulting mixture was concentrated, diluted with ethyl acetate (40 mL) and water (40 mL), then stirred overnight. The layers were separated and the organic phase was dried (Na$_2$SO$_4$) and concentrated to yield the corresponding methyl ester which was dissolved in 9:1 dioxane:water (20 mL) and treated with a solution of LiOH (1.4 g, 58 mmol). The resulting solution was stirred for 4 h then acidified to pH~3 with 1N HCl. The mixture was then extracted three times with ethyl acetate. The combined ethyl acetate extracts were washed with water, dried (Na$_2$SO$_4$) and concentrated to yield 7-(3-fluorophenoxy)-2-hydroxyheptanoic acid as a white solid. (MS m/z=257 MH+).

A solution of methyl 2-(((benzyloxy)carbonyl)amino)acetimidate (600 mg, 2.7 mmol) and 4-(benzyloxy)benzohydrazide (654 mg, 2.7 mmol) in methanol (45 mL) was heated at 80° C. in a sealed tube for 3 h. The solvent was removed under reduced pressure and the resulting residue was purified by chromatography (silica gel, heptane-ethyl acetate) to yield benzyl ((5-(4-(benzyloxy)phenyl)-1,3,4-oxadiazol-2-yl)methyl)carbamate. A solution of benzyl ((5-(4-(benzyloxy)phenyl)-1,3,4-oxadiazol-2-yl)methyl)carbamate (480 mg, 1.12 mmol) in 33% HBr in acetic acid (5 mL) was stirred for 1 h. Diethyl ether was added, and the supernatant was decanted. The process was repeated, and the resulting solid was collected by filtration to yield (5-(4-(benzyloxy)phenyl)-1,3,4-oxadiazol-2-yl)methanamine. A solution of (5-(4-(benzyloxy)phenyl)-1,3,4-oxadiazol-2-yl)methanamine (155 mg, 0.43 mmol), 7-(3-fluorophenoxy)-2-hydroxyheptanoic acid (110 mg, 0.43 mmol), 1-[3-(dimethylamino)propyl]-3-ethylcarbodiimide (99 mg, 0.52 mmol), DIPEA (0.224 mL, 1.3 mmol) and HOBt (70 mg, 0.52 mmol) in DMF (20 mL) was stirred overnight. The resulting mixture was diluted with NaHCO$_3$ (saturated, aqueous) and extracted twice with ethyl acetate. The combined extracts were washed with brine, dried (Na$_2$SO$_4$) and concentrated to yield N-((5-(4-(benzyloxy)phenyl)-1,3,4-oxadiazol-2-yl)methyl)-7-(3-fluorophenoxy)-2-hydroxyheptanamide, which was in the next step used without further purification. To a solution of N-((5-(4-(benzyloxy)phenyl)-1,3,4-oxadiazol-2-yl)methyl)-7-(3-fluorophenoxy)-2-hydroxyheptanamide (190 mg, 0.37 mmol) in methylene chloride (5 mL) was added 1,1,1-tris(acetyloxy)1,1-dihydro-1,2-benziodoxol-3-(1H)-one (233 mg, 0.55 mmol) and the resulting mixture was stirred overnight, then quenched with excess sodium thiosulfate in saturated aqueous sodium bicarbonate. The mixture was then extracted twice with ethyl acetate and the combined organic extracts were washed with brine, dried (Na$_2$SO$_4$) and concentrated. The residue was purified by chromatography (silica gel, heptane-ethyl acetate) to yield the title compound. $^1$H NMR (400 MHz, CDCl$_3$) δ 6.60-8.10 (overlapping m, 14H), 5.15 (s, 2H), 4.75-4.85 (m, 2H), 3.85-4.00 (m, 2H), 2.90-3.10 (m, 2H), 1.50-1.90 (m, 6H).

SYNTHESIS EXAMPLE 6

2-oxo-8-phenyl-N-((5-(4-(pyridin-4-ylmethoxy)phenyl)-1,3,4-thiadiazol-2-yl)methyl)octanamide Compound 140

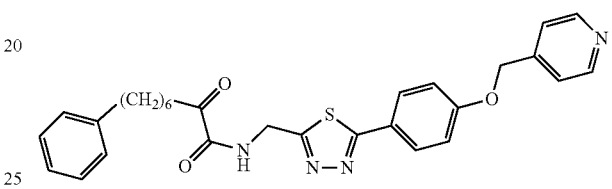

A solution of 4-(5-(aminomethyl)-1,3,4-thiadiazol-2-yl)phenol (1.74 mmol), 2-hydroxy-8-phenyloctanoic acid (1.74 mmol), HOBt (2.1 mmol), N-(3-dimethylaminopropyl)-N'-ethylcarbodiimide hydrochloride (2.1 mmol) and DIPEA (6.94 mmol) in DMF (4 mL) was stirred at room temperature overnight. The resulting mixture was diluted with NaHCO$_3$ (saturated) and extracted twice with ethyl acetate. The combined extracts were washed with brine, dried (Na$_2$SO$_4$) and concentrated. The resulting residue was purified by chromatography (silica gel, methanol-CH$_2$Cl$_2$) to yield 2-hydroxy-N-((5-(4-hydroxyphenyl)-1,3,4-thiadiazol-2-yl)methyl)-8-phenyloctanamide. A solution of 2-hydroxy-N-((5-(4-hydroxyphenyl)-1,3,4-thiadiazol-2-yl)methyl)-8-phenyloctanamide (0.18 mmol), 4-bromomethypyridine hydrochloride (0.26 mmol), and potassium carbonate (0.53 mmol) in DMF (4 mL) was stirred at room temperature overnight. The resulting mixture was diluted with ethyl acetate, washed with brine, dried (Na$_2$SO$_4$) and concentrated to yield 2-hydroxy-8-phenyl-N-((5-(4-(pyridin-4-ylmethoxy)phenyl)-1,3,4-thiadiazol-2-yl)methyl)octanamide, which was used in the next step without purification. To a solution of 2-hydroxy-8-phenyl-N-((5-(4-(pyridin-4-ylmethoxy)phenyl)-1,3,4-thiadiazol-2-yl)methyl)octanamide (0.16 mmol) in CH$_2$Cl$_2$ (5 mL) was added the Dess-Martin periodinane (0.23 mmol). The resulting mixture was stirred overnight, then quenched with an excess of a solution of sodium thiosulfate in saturated NaHCO$_3$ (aqueous). The mixture was then extracted twice with ethyl acetate and the combined extracts were washed with brine, dried (Na$_2$SO$_4$) and concentrated. The resulting residue was purified by chromatography (silica gel, heptane-ethyl acetate) to yield the title compound.

$^1$H NMR (400 MHz, CDCl$_3$) δ: 8.59-8.72 (m, 3H), 7.86-7.07 (m, 11H), 5.16 (s, 2H), 4.91 (d, 2H), 2.94 (m, 2H), 2.60 (m, 2H), 1.59-1.31 m,8H)

Additional representative compounds of the present invention were prepared according as described in Schemes 1-6 and Examples 1-6 detailed above, with mass values, as listed in Table 4, below.

TABLE 4

| ID No | Measured Mass |
|---|---|
| 1 | 392 |
| 2 | 426 |
| 3 | 422 |
| 4 | 422 |
| 5 | 426 |
| 6 | 422 |
| 7 | 436 |
| 11 | 391 |
| 12 | 410 |
| 13 | 378 |
| 15 | 410 |
| 17 | No MH+ detected |
| 18 | 426 |
| 19 | 500 |
| 20 | 428 |
| 21 | 460 |
| 22 | 460 |
| 24 | 435 |
| 25 | 406 |
| 26 | 428 |
| 27 | 442 |
| 28 | 460 |
| 30 | 460 |
| 31 | 472 |
| 32 | 436 |
| 33 | 378 |
| 34 | 428 |
| 35 | 392 |
| 36 | 504 |
| 37 | 468 |
| 38 | 446 |
| 39 | 410 |
| 40 | 404 |
| 41 | 404 |
| 42 | 393 |
| 43 | 388 |
| 44 | — |
| 45 | 413 |
| 46 | 394 |
| 47 | — |
| 48 | 444 |
| 49 | 476 |
| 50 | 477 |
| 51 | 410 |
| 52 | 486 |
| 53 | 412 |
| 54 | 462 |
| 55 | 504 |
| 56 | 504 |
| 57 | 538 |
| 58 | 484 |
| 59 | 518 |
| 60 | 486 |
| 61 | 514 |
| 62 | No MH+ detected |
| 63 | 424 |
| 64 | 516 |
| 65 | 516 |
| 66 | No MH+ |
| 67 | 538 |
| 68 | 498 |
| 69 | No MH+ detected |
| 74 | 408 |
| 75 | 577 |
| 76 | 534 |
| 77 | 534 |
| 78 | 502 |
| 80 | 516 |
| 81 | 528 |
| 82 | 499 |
| 83 | 556 |
| 84 | 516 |
| 85 | 516 |
| 86 | 499 |
| 87 | 486 |
| 88 | 499 |
| 89 | 549 |
| 90 | 534 |
| 91 | 545 |
| 92 | 522 |
| 93 | 522 |
| 94 | 536 |
| 95 | 522 |
| 96 | 535 |
| 97 | 522 |
| 98 | 522 |
| 99 | 536 |
| 100 | 536 |
| 101 | 536 |
| 102 | 522 |
| 103 | 538 |
| 104 | 539 |
| 105 | 512 |
| 106 | 502 |
| 107 | 500 |
| 108 | 446 |
| 109 | 511 |
| 110 | 547 |
| 111 | 512 |
| 115 | 597 |
| 116 | 497 |
| 117 | 523 |
| 118 | 533 |
| 119 | 503 |
| 120 | 486 |
| 121 | 517 |
| 123 | 598 |
| 124 | 498 |
| 125 | 598 |
| 126 | No MH+ detected |
| 127 | 503 |
| 128 | 532 |
| 129 | 514 |
| 130 | 500 |
| 133 | 538 |
| 134 | 537 |
| 136 | 553 |
| 137 | 572 |
| 138 | 515 |
| 139 | 515 |
| 140 | 515 |
| 141 | 562 |
| 142 | 528 |
| 143 | 482 |
| 144 | 539 |
| 145 | 532 |
| 146 | 550 |
| 147 | 584 |
| 148 | 395 |
| 149 | 506 |
| 150 | 585 |
| 151 | 533 |
| 152 | 533 |
| 154 | 553 |
| 156 | 531 |
| 157 | 590 |
| 159 | 534 |
| 161 | 533 |
| 162 | 595 |
| 163 | 540 |
| 164 | 549 |
| 165 | 551 |
| 166 | 536 |
| 167 | 534 |
| 168 | 552 |
| 169 | 569 |
| 170 | 591 |
| 171 | 412 |
| 172 | 530 |
| 173 | 549 |
| 174 | 529 |
| 175 | 534 |
| 176 | 501 |
| 177 | 393 |

TABLE 4-continued

| ID No | Measured Mass |
|---|---|
| 178 | 393 |
| 179 | 484 |

BIOLOGICAL EXAMPLE 1

Endothelial Lipase Assay (Human/Mouse)

To assay for cell surface lipase activity, cells expressing human endothelial lipase (EL) or LPL were plated in Cell-BIND® 384-well plates (Corning, Lowell, Mass.) in 25 µL serum free medium at a density of 2000 cells/well. After 18-24 hours incubation at 37° C., the medium was removed and replaced with 15 µL assay buffer [Hank's Buffered Saline Solution with 25 mM HEPES pH 7.2] and 15 µL $PLA_1$ for a final concentration of 10 µM using a Multidrop reagent dispenser. Fluorescence signal was monitored for 30 min at 37° C. on a Safire II plate reader in kinetic mode (60 cycles, kinetic interval: 30 seconds) with an excitation wavelength of 490 nm and an emission wavelength of 515 nm. Linear regression of the fluorescence intensity collected from 480 to 1500 seconds was used to calculate the reaction rate (the slope) and the slopes were used to calculate $IC_{50}$ values where appropriate. The amount of BODIPY-labeled product generated was calculated at the 30 min time point as determined from standard curve analysis of purified BODIPY FL $C_5$. In all studies using the inhibitor Ebelactone B, consistent results were obtained when it was dissolved as a stock in DMSO, immediately before use.

Representative compounds of the present invention (prepared as described in the schemes outlined herein) were tested according to the procedures as described above, with calculated $IC_{50}$ values (in µM) as listed in Table 5, below.

TABLE 5

| | Mouse and Human EL $IC_{50}$ | |
|---|---|---|
| ID No | Human $IC_{50}$ (µM) | Mouse $IC_{50}$ (µM) |
| 1 | 0.952, 0.836, 0.690 | 1.054, 0.864, 0.708 |
| 2 | 0.488 | 0.616 |
| 3 | 1.096 | |
| 4 | 0.640 | |
| 5 | 0.663 | |
| 6 | 2.648 | |
| 7 | 0.457 | |
| 11 | 10.435 | |
| 12 | 2.102 | 1.757 |
| 13 | 0.915 | 0.662 |
| 15 | 0.735 | 1.021 |
| 17 | 3.361 | 1.880 |
| 18 | 0.440 | 0.346 |
| 19 | 5.376 | 3.054 |
| 20 | 0.490 | 0.552 |
| 21 | 0.684 | 0.654 |
| 22 | 0.268, 0.552 | 0.435, 0.396 |
| 24 | 16.554 | 20.682 |
| 25 | 0.353, 0.319, 0.468 | 0.333, 0.235, 0.269 |
| 26 | 0.668 | 0.436 |
| 27 | 0.293, 0.129 | 0.225, 0.184 |
| 28 | 0.224 | 0.127 |
| 30 | 0.523 | 0.205 |
| 31 | 0.141 | 0.120 |
| 32 | 0.213 | 0.165 |
| 33 | 3.758 | 3.351 |
| 34 | 0.904 | 0.473 |
| 35 | 1.133 | 0.994 |
| 36 | 10.186 | 6.600 |

TABLE 5-continued

| | Mouse and Human EL $IC_{50}$ | |
|---|---|---|
| ID No | Human $IC_{50}$ (µM) | Mouse $IC_{50}$ (µM) |
| 37 | 2.531 | 1.473 |
| 38 | 0.613 | 0.475 |
| 39 | 0.643 | 0.772 |
| 40 | 33.335 | 33.335 |
| 41 | 27.171 | 24.138 |
| 42 | 4.648 | 2.728 |
| 43 | 2.414 | 2.650 |
| 44 | 0.951 | 0.641 |
| 45 | 3.471 | 2.410 |
| 46 | 8.754 | 6.513 |
| 47 | 3.188 | 3.027 |
| 48 | 1.962 | 1.709 |
| 49 | 0.561 | 0.312 |
| 50 | 0.564 | 0.267 |
| 51 | 0.607 | 0.802 |
| 52 | 2.607 | 1.798 |
| 53 | 4.737 | 5.910 |
| 54 | 0.916 | 0.802 |
| 55 | 0.340 | 0.384 |
| 56 | 3.249 | 2.292 |
| 57 | 3.780 | 1.095 |
| 58 | 4.888 | 1.718 |
| 59 | 2.590 | 1.113 |
| 60 | 7.124 | 9.795 |
| 61 | 2.356 | 0.966 |
| 62 | 5.200 | 2.723 |
| 63 | 5.454 | 6.116 |
| 64 | 10.884 | 9.975 |
| 65 | 0.872 | 0.793 |
| 66 | 0.255 | 0.366 |
| 67 | 0.640 | 0.648 |
| 68 | 0.142 | 0.124 |
| 69 | 0.272 | 0.835 |
| 74 | 0.219 | 0.436 |
| 75 | 11.564 | 11.220 |
| 76 | 3.073 | 1.947 |
| 77 | 33.335 | 33.335 |
| 78 | 0.9445 | 0.775 |
| 80 | 0.600 | 0.214 |
| 81 | 11.545 | 8.341 |
| 82 | 0.108 | 0.133 |
| 83 | 0.121 | 0.064 |
| 84 | 0.235 | 0.200 |
| 85 | 0.223 | 0.169 |
| 86 | 0.156 | 0.072 |
| 87 | 1.448 | 0.708 |
| 88 | 0.178 | 0.196 |
| 89 | 0.565 | 0.232 |
| 90 | 0.548, 0.1883 | 0.080, 0.159 |
| 91 | 0.340 | 0.174 |
| 92 | 0.432 | 0.911 |
| 93 | 3.059 | 1.485 |
| 94 | 0.936 | 0.634 |
| 95 | 1.056 | 0.560 |
| 96 | 1.297 | 0.666 |
| 97 | 1.803 | 0.457 |
| 98 | 1.731 | 0.774 |
| 99 | 2.154 | 1.048 |
| 100 | 1.327 | 0.551 |
| 101 | 5.478 | 19.930 |
| 102 | 1.966 | 0.809 |
| 103 | 1.961 | 2.746 |
| 104 | 0.230 | 0.181 |
| 105 | 0.139 | 0.048 |
| 106 | 0.746 | 0.298 |
| 107 | 0.345 | 0.216 |
| 108 | 0.626 | 1.170 |
| 109 | 0.505 | 0.317 |
| 110 | 0.677 | 0.346 |
| 111 | 0.236 | 0.156 |
| 115 | 0.515 | 0.254 |
| 116 | 0.325 | 0.289 |
| 117 | 0.078 | 0.050 |
| 118 | 0.675 | 0.476 |
| 119 | 0.979 | 0.904 |
| 120 | 1.508 | 0.973 |

TABLE 5-continued

Mouse and Human EL IC$_{50}$

| ID No | Human IC$_{50}$ (μM) | Mouse IC$_{50}$ (μM) |
|---|---|---|
| 121 | 0.471 | 0.187 |
| 123 | 0.288 | 0.182 |
| 124 | 3.612 | 2.928 |
| 125 | 2.575 | 0.993 |
| 126 | 0.398 | 0.242 |
| 127 | 0.308 | 0.281 |
| 128 | 0.129 | 0.087 |
| 129 | 0.325 | 0.264 |
| 130 | 0.111 | 0.080 |
| 133 | 0.386 | 0.176 |
| 134 | 0.604 | 0.243 |
| 136 | 0.595 | 0.406 |
| 137 | 0.093 | 0.037 |
| 138 | 0.055, 0.108 | 0.058, 0.079 |
| 139 | 0.071 | 0.042 |
| 140 | 0.032 | 0.029 |
| 141 | 0.101 | 0.045 |
| 142 | 1.576 | 0.897 |
| 143 | 7.686 | 11.069 |
| 144 | 0.421 | 0.249 |
| 145 | 0.312 | 0.168 |
| 146 | 2.322 | 0.224 |
| 147 | 0.623 | 0.057 |
| 148 | 12.337 | 14.726 |
| 149 | 4.253 | 3.405 |
| 150 | 0.092 | 0.048 |
| 151 | 0.712 | 0.661 |
| 152 | 0.115, 0.042 | 0.207, 0.048 |
| 154 | 0.036 | 0.047 |
| 156 | 0.397 | 0.383 |
| 157 | 0.511 | 1.280 |
| 159 | 0.240 | 0.174 |
| 161 | 0.093 | 0.037 |
| 162 | 1.340 | 0.202 |
| 163 | 0.974 | 0.236 |
| 164 | 0.751 | 0.232 |
| 165 | 0.048 | 0.048 |
| 166 | 0.809 | 0.479 |
| 167 | 0.360 | 0.217 |
| 168 | 0.107 | 0.064 |
| 169 | 0.085 | 0.062 |
| 170 | 0.016 | 0.014 |
| 171 | 33.000 | |
| 172 | 32.000 | |
| 173 | 0.037 | 0.017 |
| 174 | 0.078 | 0.051 |
| 175 | 1.292 | 4.407 |
| 176 | 27.893 | 26.984 |
| 177 | 5.218 | |
| 178 | 11.641 | 7.322 |
| 179 | 0.247 | 0.135 |

BIOLOGICAL EXAMPLE 2

Representative compounds of the present invention were additionally tested for inhibition of LPL (lipoprotein lipase) and HL (hepatic lipase) and found to be selective for their inhibition of EL over LPL.

FORMULATION EXAMPLE 1 (PROPHETIC EXAMPLE)

Solid Oral Dosage Pharmaceutical Composition

As a specific embodiment of an oral composition, 100 mg of a compound of formula (I) as herein described is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

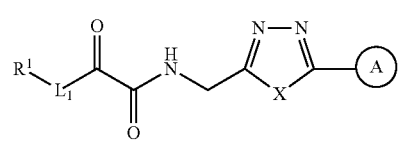

wherein
R$^1$ is an aromatic ring selected from the group consisting of phenyl, pyridyl, pyrimidinyl, thiazolyl, and quinolinyl; wherein the aromatic ring is optionally substituted with one to two substituents independently selected from the group consisting of halogen, C$_{1-4}$alkyl, trifluoromethyl, C$_{1-4}$alkoxy, trifluoromethoxy, cyano, —C(O)—NR$^A$R$^B$, —NH—C(O)—(C$_{1-4}$alkyl), and phenyl; and wherein R$^A$ and R$^B$ are each independently selected from the group consisting of hydrogen and C$_{1-4}$ alkyl;

L$^1$ is selected from the group consisting of -(n-pentyl)-, -(n-hexyl)-, —O—(n-pentyl)-, —NH-(n-pentyl)-, —CH═CH-(n-propyl)-, —CH═CH-(n-butyl)-, —CC-(n-propyl)- and —CC-(n-butyl)-;

X is selected from the group consisting of —NH—, —O— and —S—;

is selected from the group consisting of
(a)

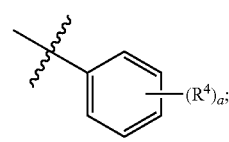

a is an integer from 0 to 2;
each R$^4$ is independently selected from the group consisting of halogen, C$_{1-4}$alkyl, trifluoromethoxy, NR$^6$R$^7$, —C(O)—NH—CH$_2$CH$_2$—NR$^6$R$^7$ and phenyl; wherein R$^6$ and R$^7$ are each independently selected form the group consisting of hydrogen and C$_{1-4}$alkyl;
wherein the R$^4$ phenyl is optionally substituted with one to three substituents independently selected from the group consisting of halogen, C$_{1-4}$alkyl, trifluoromethyl, C$_{1-4}$alkoxy and trifluoromethoxy;
(b)

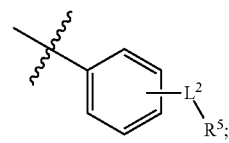

L² is selected from the group consisting of —O—, —NR⁷— and —S(O)—; wherein R⁷ is selected from the group consisting of hydrogen, C₁₋₄alkyl and t-butoxycarbonyl;

R⁵ is an aromatic ring structure selected from the group consisting of phenyl, benzyl, phenylethyl-, imidazolyl, imidazolyl-methyl-, pyridyl, pyridyl-methyl-, pyrimidinyl, pyrimidinyl-methyl-, furyl, furylmethyl-, quinolinyl, quinolinyl-methyl-, benzo[d][1,2,3]triazolyl and benzo[d][1,2,3]triazolyl-methyl-;

wherein the R⁵ aromatic ring structure is optionally substituted with one to two substituents independently selected from the group consisting of halogen, C₁₋₄alkyl, trifluoromethyl, C₁₋₄alkoxy, trifluoromethoxy, —C(O)OH, —C(O)—O—C₁₋₄alkyl, cyano, and —C(O)—NR⁸R⁹; wherein R⁸ and R⁹ are each independently selected from the group consisting of hydrogen and C₁₋₄alkyl;

alternatively R⁵ is 4-(pyrid-4-yl-N-oxide-methoxy)-phenyl;

and wherein the -L²-R⁵ group is bound at the 3- or 4-position;

(c) naphth-2-yl; and (d) a heteroaryl selected from the group consisting of pyridyl, benzo[d][1,3]dioxolyl, dibenzo[b,e][1,4]dioxinyl, and 2,3-dihydropyrrolo[2,1-b]quinazolin-9-one;

or a pharmaceutically acceptable salt thereof.

2. A compound as in claim 1, wherein

R¹ is an aromatic ring selected from the group consisting of phenyl, pyridyl, pyrimidinyl, thiazolyl, and quinolinyl;

wherein the aromatic ring is optionally substituted with one to two substituents independently selected from the group consisting of halogen, C₁₋₄alkyl, trifluoromethyl, C₁₋₄alkoxy, trifluoromethoxy, cyano, —C(O)—NRᴬRᴮ, —NH—C(O)—(C₁₋₄alkyl) and phenyl; and wherein Rᴬ and Rᴮ are each independently selected from the group consisting of hydrogen and C₁₋₂alkyl;

L¹ is selected from the group consisting of -(n-pentyl)-, -(n-hexyl)-, —O—(n-pentyl)-, —NH-(n-pentyl)-, —CH═CH-(n-butyl)-, —CC-(n-propyl)- and —CC-(n-butyl)-;

X is selected from the group consisting of —NH—, —O— and —S—;

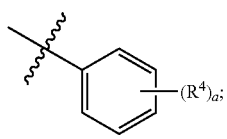

is selected from the groin consisting of (a)

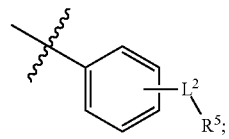

wherein a is an integer from 0 to 2;

each R⁴ is independently selected from the group consisting of halogen, C₁₋₄alkyl, trifluoromethyl, C₁₋₄alkoxy, trifluoromethoxy, —NR⁶R⁷, —C(O)—NH—CH₂CH₂—NR⁶R⁷ and phenyl; wherein R⁶ and R⁷ are each independently selected from the group consisting of hydrogen and C₁₋₄alkyl;

(b)

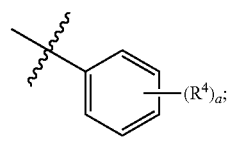

L² is selected from the group consisting of —O—, —NR⁷— and —S(O)—; wherein R⁷ is selected from the group consisting of hydrogen, C₁₋₄alkyl and t-butoxycarbonyl;

R⁵ is an aromatic ring structure selected from the group consisting of phenyl, benzyl, phenylethyl-, imidazolyl-methyl-, pyridyl-methyl-, pyrimidinyl-methyl-, furyl-methyl-, quinolinyl-methyl- and benzo[d][1,2,3]triazolyl-methyl-;

wherein the R⁵ aromatic ring structure is optionally substituted with one to two substituents independently selected from the group consisting of halogen, C₁₋₄alkyl, trifluoromethyl, C₁₋₄alkoxy, trifluoromethoxy, —C(O)OH, —C(O)—O—C₁₋₄alkyl, cyano, and —C(O)—NR⁸R⁹; wherein R⁸ and R⁹ are each independently selected from the group consisting of hydrogen and C₁₋₄alkyl;

alternatively R⁵ is 4-(pyrid-4-yl-N-oxide-methoxy)-phenyl;

and wherein the -L²-R⁵ group is bound at the 3- or 4-position;

(c) naphth-2-yl; and (d) a heteroaryl selected from the group consisting of pyridyl, benzo[d][1,3]dioxolyl, dibenzo[b,e][1,4]dioxinyl and 2,3-dihydropyrrolo[2,1-b]quinazolinone;

or a pharmaceutically acceptable salt thereof.

3. A compound as in claim 2, wherein

R¹ is an aromatic ring selected from the group consisting of phenyl, pyridyl, pyrimidinyl, thiazolyl and quinolinyl;

wherein the aromatic ring is optionally substituted with one to two substituents independently selected from the group consisting of halogen, C₁₋₂alkyl, trifluoromethyl, C₁₋₂alkoxy, cyano, —C(O)—NH₂, —NH—C(O)—(C₁₋₂alkyl) and phenyl;

L¹ is selected from the group consisting of -(n-pentyl)-, -(n-hexyl)-, —O-(n-pentyl)-, —NH-(n-pentyl)-, —CH═CH-(n-butyl)-, —CC-(n-propyl)- and —CC-(n-butyl)-;

X is selected from the group consisting of —NH—, —O— and —S—;

is selected from the group consisting of (a)

wherein a is an integer from 0 to 2;

and wherein each $R^4$ is independently selected from the group consisting of halogen, $C_{1-2}$alkyl, trifluoromethyl, $C_{1-2}$alkoxy, —$NR^6R^7$, —C(O)—NH-CH$_2$CH$_2$-$NR^6R^7$ and phenyl; wherein $R^6$ and $R^7$ are each independently selected from the group consisting of hydrogen and $C_{1-2}$alkyl;

(b)

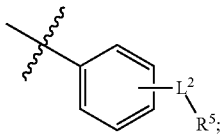

wherein $L^2$ is selected from the group consisting of —O—, —$NR^7$— and —S(O)—; wherein $R^7$ is selected from the group consisting of hydrogen, $C_{1-2}$alkyl and t-butoxycarbonyl;

$R^5$ is an aromatic ring structure selected from the group consisting of phenyl, benzyl, phenylethyl-, imidazolyl-methyl-, pyridyl-methyl-, pyrimidinyl-methyl-, furyl-methyl-, quinolinyl-methyl- and benzo[d][1,2,3]triazolyl-methyl-;

wherein the $R^5$ aromatic ring structure is optionally substituted with one to two substituents independently selected from the group consisting of halogen, $C_{1-2}$alkyl, $C_{1-2}$alkoxy, —C(O)OH, —C(O)O—$C_{1-4}$alkyl, cyano, and —C(O)—$NR^8R^9$; wherein $R^8$ and $R^9$ are each independently selected from the group consisting of hydrogen and $C_{1-2}$alkyl;

alternatively $R^5$ is 4-(pyrid-4-yl-N-oxide-methoxy)-phenyl;

and wherein the -$L^2$-$R^5$ group is bound at the 3- or 4-position;

(c) naphth-2-yl; and (d) a heteroaryl selected from the group consisting of pyridyl, benzo[d][1,3]dioxol-5-yl, dibenzo[b,e][1,4]dioxin-2-yl and 6-(2,3-dihydropyrrolo[2,1-b]quinazolin-9-one);

or a pharmaceutically acceptable salt thereof.

4. A compound as in claim 3, wherein $R^1$ is selected from the group consisting of phenyl, 3-methoxy-phenyl, 4-methoxy-phenyl, 2-fluoro-phenyl, 3-fluoro-phenyl, 4-fluoro-phenyl, 3-chloro-phenyl, 4-cyano-phenyl, 3-trifluoromethyl-phenyl, 2,3-difluoro-phenyl, 2,4-difluoro-phenyl, 2,5-difluoro-phenyl, 2,6-difluoro-phenyl, 3,5-difluoro-phenyl, 4-biphenyl, pyrid-4-yl, 2-fluoro-pyrid-3-yl, 6-fluoro-pyrid-2-yl, 6-fluoro-pyrid-3-yl, 6-trifluoromethyl-pyrid-3-yl, 5-aminocarbonyl-pyrid-3y1, 6-(methylcarbonylamino)-pyrid-3-yl, pyrimidin-2-yl, 4-methyl-thiazol-5-yl and 2-chloro-quinolin-6-yl;

$L^1$ is selected from the group consisting of -(n-pentyl)-, -(n-hexyl)-, —O-(n-pentyl)-, —NH-(n-pentyl)-, —CH=CH-(n-butyl)-, —CC-(n-propyl)- and —CC-(n-butyl)-;

X is selected from the group consisting of —NH—, —O— and —S—;

is selected from the group consisting of (a) phenyl, 2-fluoro-phenyl, 3-fluoro-phenyl, 4-fluoro-phenyl, 3,4-difluoro-phenyl, 3,5-difluoro-phenyl, 2-chloro-phenyl, 3-chloro-phenyl, 4-chlorophenyl, 4-methyl-phenyl, 2-methoxy-phenyl, 3-methoxy-phenyl, 4-methoxy-phenyl, 3-trifluoromethyl-phenyl, 4-trifluoromethyl-phenyl, 4-dimethylamino-phenyl and 4-(dimethylamino-ethylamino-carbonyl)-phenyl;

(b) 3-phenoxy-phenyl, 4-phenoxy-phenyl, 4-(3-chloro-phenoxy)-phenyl, 4-(4-chloro-phenoxy)-phenyl, 4-(4-fluoro-phenoxy)-phenyl, 4-benzyloxy-phenyl, 4-(2-fluoro-benzyloxy)-phenyl, 4-(3-fluoro-benzyloxy)-phenyl, 4-(4-fluoro-benzyloxy)-phenyl, 4-(3,5-difluoro-benzyloxy)-phenyl, 4-(4-methoxy-benzyloxy)-phenyl, 4-(3-cyano-benzyloxy)-phenyl, 4-(3-carboxy-benzyloxy)-phenyl, 4-(3-methoxycarbonyl-benzyloxy)-phenyl, 4-(3-t-butoxycarbonyl-benzyloxy)-phenyl, 4-(3-dimethylamino-carbonyl-benzyloxy)-phenyl, 4-(phenyl-ethoxy)-phenyl, 4-(N-methyl-N-(4-bromophenyl)-amino)-phenyl, 4-(N-benzyl-amino)-phenyl, 4-(N-methyl-N-benzyl-amino)-phenyl, 4-(N-(3,4-difluorobenzyl)-amino)-phenyl, 4-(N-methyl-N-(3,4-difluorobenzyl)-amino)-phenyl, 4-(N-methyl-N-(pyrid-2-ylmethyl)-amino)-phenyl, 4-(N-benzyl-N-4-butoxycarbonyl)-amino)-phenyl, 4-(N-(3,4-difluorobenzyl)-amino)-phenyl, 4-(N-(pyrid-3-yl-methyl)-amino)-phenyl, 4-(N-t-butoxycarbonyl-N-(pyrid-3-yl-methyl)-amino)-phenyl, 4-(pyrid-2-yl-methoxy)-phenyl, 4-(pyrid-3-yl-methoxy)-phenyl, 4-(pyrid-4-yl-methoxy)-phenyl, 4-(2-fluoro-pyrid-2-yl-methoxy)-phenyl, 4-(3-fluoro-pyrid-2-yl-methoxy)-phenyl, 4-(6-fluoro-pyrid-2-yl-methoxy)-phenyl, 4-(6-chloro-pyrid-2-yl-methoxy)-phenyl, 4-(3-fluoro-pyrid-4-yl-methoxy)-phenyl,4-(5-fluoro-pyrid-3-yl-methoxy)-phenyl, 4-(2-fluoro-pyrid-4-yl-methoxy)-phenyl, 4-(2-chloro-pyrid-4-yl-methoxy)-phenyl, 4-(3-fluoro-pyrid-4-yl-methoxy)-phenyl, 4-(2,6-dichloro-pyrid-4-yl-methoxy)-phenyl, 4-(6-bromo-pyrid-2-yl-methoxy)-phenyl, 4-(2-methyl-pyrid-4-yl-methoxy)-phenyl, 4-(6-cyano-pyrid-2-yl-methoxy)-phenyl, 4-(1-methyl-imidazol-2-yl-methoxy)-phenyl, 4-(pyrimidin-2-yl-methoxy)-phenyl, 4-(pyrimidin-4-yl-methoxy)-phenyl, 4-(quinolin-2-yl-methoxy)-phenyl, 4-(5-methoxycarbonyl-fur-2-yl-methoxy)-phenyl, 4-(1H-benzo[d]1,2,3]triazol-1-yl-methoxy)-phenyl, 4-(benzyl-sulfonyl)-phenyl, 4-(pyrid-4-yl-N-oxide-methoxy)-phenyl;

(c) naphth-2-yl; and (d) pyrid-3-yl, pyrid-4-yl, benzo[d][1,3]dioxo1-5-yl, dibenzo[b,e][1,4]dioxin-2-yl and 6-(2,3-dihydropyrrolo[2,1-b]quinazolin-9-one);

or a pharmaceutically acceptable salt thereof.

5. A compound as in claim 4, wherein $R^1$ is selected from the group consisting of phenyl, 3-methoxy-phenyl, 3-fluoro-phenyl, 4-fluoro-phenyl, 2,4-difluoro-phenyl, 3,5-difluoro-phenyl, 6-fluoro-pyrid-3-yl, 6-(methylcarbonylamino)-pyrid-3-yl and 4-methyl-thiazol-5-yl;

$L^1$ is selected from the group consisting of -(n-hexyl)- and —O-(n-pentyl)-;

X is selected from the group consisting of —O— and —S—;

is selected from the group consisting of
(a) phenyl, 3,4-difluoro-phenyl, 3-chloro-phenyl, 4-chloro-phenyl, 4-methyl-phenyl and 4-trifluoromethyl-phenyl;
(b) 4-phenoxy-phenyl, 4-(3-chloro-phenoxy)-phenyl, 4-benzyloxy-phenyl, 4-(2-fluoro-benzyloxy)-phenyl, 4-(3-fluoro-benzyloxy)-phenyl, 4-(3,5-difluoro-benzyloxy)-phenyl, 4-(3-cyano-benzyloxy)- phenyl, 4-(3-methoxycarbonyl-benzyloxy)-phenyl, 4-(3-dimethylamino-carbonyl-benzyloxy)-phenyl, 4-(phenyl-ethoxy)-phenyl, 4-(N-benzyl-amino)-phenyl, 4-(N-methyl-N-benzyl-amino)-phenyl, 4-(N-methyl-N-(pyrid-2-ylmethyl)-amino)-phenyl, 4-(N-benzyl-N-4-butoxycarbonyl)-amino)-phenyl, 4-(N-t-butoxycarbonyl-N-(pyrid-3-yl-methyl)-amino)-phenyl, 4-(pyrid-2-yl-methoxy)-phenyl, 4-(pyrid-3-yl-methoxy)-phenyl, 4-(pyrid-4-yl-methoxy)-phenyl, 4-(6-fluoro-pyrid-2-yl-methoxy)-phenyl, 4-(3-fluoro-pyrid-4-yl-methoxy)-phenyl, 4-(2-fluoro-pyrid-4-yl-methoxy)-phenyl, 4-(2-chloro-pyrid-4-yl-methoxy)-phenyl, 4-(2-methyl-pyrid-4-yl-methoxy)-phenyl, 4-(pyrimidin-4-yl-methoxy)-phenyl, 4-(5-methoxycarbonyl-fur-2-yl-methoxy)-phenyl, 4-(1 H-benzo [d] 1,2,3 ]triazol-1-yl-methoxy)-phenyl, -(pyrid-4-yl-N-oxide-methoxy)-phenyl;
(c) naphth-2-yl; and
(d) benzo[d][1,3]dioxol-5-yl;
or a pharmaceutically acceptable salt thereof.

6. A compound as in claim 5, wherein $R^1$ is selected from the group consisting of phenyl, 3-methoxy-phenyl, 3-fluoro-phenyl, 6-fluoro-pyrid-3-yl and 4-methyl-thiazol-5-yl;
$L^1$ is -(n-hexyl)-;
X is selected from the group consisting of —O— and —S—;

(A)

is selected from the group consisting of
(a) phenyl and 4-methyl-phenyl;
(b) 4-phenoxy-phenyl, 4-(3-chloro-phenoxy)-phenyl, 4-benzyloxy-phenyl, 4-(2-fluoro-benzyloxy)-phenyl, 4-(3-fluoro-benzyloxy)-phenyl, 4-(3-cyano-benzyloxy)-phenyl, 4-(3-methoxycarbonyl-benzyloxy)-phenyl, 4-(3-dimethylamino-carbonyl-benzyloxy)-phenyl, 4-(phenyl-ethoxy)-phenyl, 4-(N-methyl-N-(pyrid-2-yl-methyl)-amino)-phenyl, 4-(pyrid-2-yl-methoxy)-phenyl, 4-(pyrid-3-yl-methoxy)-phenyl, 4-(pyrid-4-yl-methoxy)-phenyl, 4-(3-fluoro-pyrid-4-yl-methoxy)-phenyl, 4-(2-fluoro-pyrid-4-yl-methoxy)-phenyl, 4-(2-chloro-pyrid-4-yl-methoxy)-phenyl, 4-(2-methyl-pyrid-4-yl-methoxy)-phenyl, 4-(5-methoxycarbonyl-fur-2-yl-methoxy)-phenyl, 4-(1H-benzo[d]1,2,3] triazol-1-yl-methoxy)-phenyl; and
(c) naphth-2-yl;
or a pharmaceutically acceptable salt thereof.

7. A compound as in claim 6, wherein $R^1$ is selected from the group consisting of phenyl, 6-fluoro-pyrid-3-yl and 4-methyl-thiazol-5-yl;
$L^1$ is -(n-hexyl)- ;
X is selected from the group consisting of —O— and —S—;

(A)

is selected from the group consisting of (b) 4-phenoxy-phenyl, 4-(3-fluoro-benzyloxy)-phenyl, 4-(3-cyano-benzyloxy)-phenyl, 4- (3-methoxycarbonyl-benzyloxy)-phenyl, 4-(3-dimethylamino-carbonyl-benzyloxy)-phenyl, 4-(pyrid-2-yl-methoxy)-phenyl, 4-(pyrid-3-yl-methoxy)-phenyl, 4-(pyrid-4-yl-methoxy)-phenyl, 4-(3-fluoro-pyrid-4-yl-methoxy)-phenyl, 4-(2-fluoro-pyrid-4-yl-methoxy)-phenyl, 4-(2-chloro-pyrid-4-yl-methoxy)-phenyl, 4-(2-methyl-pyrid-4-yl-methoxy)-phenyl and 4-(5-methoxycarbonyl-fur-2-yl-methoxy)-phenyl;
or a pharmaceutically acceptable salt thereof.

8. A compound as in claim 7, wherein
$R^1$ is selected from the group consisting of phenyl, 6-fluoro-pyrid-3-yl and 4-methyl-thiazol-5-yl;
$L^1$ is -(n-hexyl)-;
X is —S—;

(A)

is selected from the group consisting of (b) 4-(3-fluoro-benzyloxy)-phenyl, 4-(3-methoxycarbonyl-benzyloxy)-phenyl, 4-(pyrid-4-yl-methoxy)-phenyl and 4-(2-chloro-pyrid-4-yl-methoxy)-phenyl;
or a pharmaceutically acceptable salt thereof.

9. A compound as in claim 1 wherein (A)

is

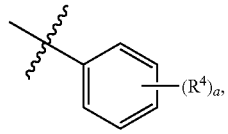

selected from the group, consisting of:

| $R^1$ | $L^1$ | X | $(R^4)_a$ |
|---|---|---|---|
| phenyl | -n-hexyl- | O | a = 0 |
| phenyl | -n-hexyl- | O | 4-chloro |
| phenyl | -n-hexyl- | O | 3-methoxy |
| phenyl | -n-hexyl- | O | 4-methoxy |
| phenyl | -n-hexyl- | O | 2-chloro |
| phenyl | -n-hexyl- | O | 2-methoxy |
| phenyl | -n-hexyl- | NH | a = 0 |
| phenyl | -n-hexyl- | O | 2-fluoro |
| phenyl | -n-hexyl- | O | 3-fluoro |
| phenyl | -n-hexyl- | O | 4-fluoro |
| phenyl | -n-hexyl- | O | 4-phenyl |
| phenyl | -n-hexyl- | O | 3-chloro |
| phenyl | -n-hexyl- | O | 3,4-difluoro |
| phenyl | -n-hexyl- | O | 3-trifluoromethyl |
| phenyl | -n-hexyl- | O | 4-trifluoromethyl |

-continued

| R¹ | L¹ | X | (R⁴)ₐ |
|---|---|---|---|
| phenyl | -n-hexyl- | O | 4-dimethylamino |
| phenyl | -n-hexyl- | O | 4-methyl |
| phenyl | -n-hexyl- | O | 3,5-difluoro |
| 3-methoxy-phenyl | -n-hexyl- | O | 4-methyl |
| phenyl | -n-pentyl- | O | a = 0 |
| phenyl | -n-pentyl- | O | 4-methyl |
| 4-biphenyl | -n-pentyl- | O | 4-methyl |
| 4-fluoro-phenyl | -n-pentyl- | O | 4-methyl |
| 3-methoxy-phenyl | —CC—(CH₂)₃— | O | a = 0 |
| 4-methoxy-phenyl | —CC—(CH₂)₃— | O | a = 0 |
| pyrid-4-yl | -n-hexyl- | O | a = 0 |
| phenyl | —CC—(CH₂)₄— | O | a = 0 |
| 4-cyano-phenyl | -n-hexyl- | O | a = 0 |
| 4-cyano-phenyl | —CC—(CH₂)₄— | O | a = 0 |
| phenyl | —O-n-pentyl- | O | a = 0 |
| phenyl | —O-n-pentyl- | O | 4-methyl |
| 3-trifluoro-methoxy-phenyl | -n-hexyl- | O | a = 0 |
| 2-chloro-quinolin-6-yl | -n-hexyl- | O | a = 0 |
| 2-fluoro-phenyl | -n-hexyl- | O | a = 0 |
| 3-fluoro-phenyl | —O-n-pentyl- | O | a = 0 |
| 3-methoxy-phenyl | —O-n-pentyl- | O | a = 0 |
| phenyl | -n-hexyl- | S | a = 0 |
| 3,5-difluoro-phenyl | —O-n-pentyl- | S | a = 0 |
| pyrimidin-2-yl | —NH-n-pentyl- | O | a = 0 |
| phenyl | -n-hexyl- | O | 4-(dimethylamino-ethylamino-carbonyl) |
| 6-fluoro-pyrid-2-yl | —NH-n-pentyl- | O | a = 0 | and pharmaceutically acceptable salts thereof.

10. A compound as in claim 1, wherein

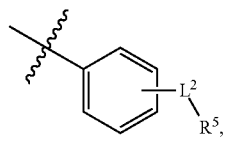

is selected from the group consisting of:

| R¹ | L¹ | X | —L²—R⁵ |
|---|---|---|---|
| phenyl | —O-n-pentyl- | O | 4-phenoxy |
| 3-fluoro-phenyl | —O-n-pentyl- | O | 4-phenoxy |
| 3-fluoro-phenyl | —O-n-pentyl- | O | 3-phenoxy |
| 3-fluoro-phenyl | —O-n-pentyl- | O | 4-(4-chloro-phenoxy) |
| phenyl | -n-hexyl- | O | 3-phenoxy |
| phenyl | -n-hexyl- | O | 4-(4-chloro-phenoxy) |
| phenyl | —O-n-pentyl- | O | 3-phenoxy |
| 3-methoxy-phenyl | —O-n-pentyl- | O | 3-phenoxy |
| 3-methoxy-phenyl | —O-n-pentyl- | O | 4-phenoxy |
| phenyl | -n-hexyl- | O | 4-(3-chloro-phenoxy) |
| 3-fluoro-phenyl | —O-n-pentyl- | O | 4-(3-chloro-phenoxy) |
| phenyl | -n-hexyl- | O | 4-benzyloxy |
| 3-fluoro-phenyl | —O-n-pentyl- | O | 4-benzyloxy |
| phenyl | -n-hexyl- | O | 4-(N-methyl-N-(4-bromophenyl)-amino) |
| phenyl | -n-hexyl- | O | 4-(3-chloro-benzyloxy) |
| phenyl | -n-hexyl- | O | 4-(4-chloro-benzyloxy) |
| phenyl | -n-hexyl- | O | 4-(1-methyl-imidazol-2-yl-methoxy) |
| phenyl | -n-hexyl- | O | 4-(4-fluoro-benzyloxy) |
| phenyl | -n-hexyl- | O | 4-(4-methoxy-benzyloxy) |
| phenyl | -n-hexyl- | O | 4-(pyrid-3-yl-methoxy) |
| phenyl | -n-hexyl- | O | 4-(3-methoxycarbonyl-benzyloxy) |
| phenyl | -n-hexyl- | O | 4-(3-fluoro-benzyloxy) |
| phenyl | -n-hexyl- | O | 4-(2-fluoro-benzyloxy) |
| phenyl | -n-hexyl- | O | 4-(pyrid-4-yl-methoxy) |
| phenyl | -n-hexyl- | O | 4-(pyrimidin-2-yl-oxy) |
| phenyl | -n-hexyl- | O | 4-(pyrid-2-yl-methoxy) |
| phenyl | -n-hexyl- | O | 4-(quinolin-2-yl-methoxy) |
| phenyl | -n-hexyl- | O | 4-(3,5-difluoro-benzyloxy) |
| phenyl | -n-hexyl- | O | 4-(5-methoxycarbonyl-fur-2-yl-methoxy) |
| 2,4-difluoro-phenyl | —O-n-pentyl- | O | 4-phenoxy |
| 2,6-difluoro-phenyl | —O-n-pentyl- | O | 4-phenoxy |
| 2,5-difluoro-phenyl | —O-n-pentyl- | O | 4-benzyloxy |
| 3,5-difluoro-phenyl | —O-n-pentyl- | O | 4-phenoxy |
| 3-chloro-phenyl | —O-n-pentyl- | O | 4-benzyloxy |
| 3-chloro-phenyl | —O-n-pentyl- | O | 4-phenoxy |
| 2,5-difluoro-phenyl | —O-n-pentyl- | O | 4-phenoxy |
| 2,4-difluoro-phenyl | —O-n-pentyl- | O | 4-benzyloxy |
| 3,5-difluoro-phenyl | —O-n-pentyl- | O | 4-benzyloxy |
| 2,6-difluoro-phenyl | —O-n-pentyl- | O | 4-benzyloxy |
| 2,3-difluoro-phenyl | —O-n-pentyl- | O | 4-phenoxy |
| 2,3-difluoro-phenyl | —O-n-pentyl- | O | 4-benzyloxy |

-continued

| R¹ | L¹ | X | —L²—R⁵ |
|---|---|---|---|
| phenyl | -n-hexyl- | O | 4-(1H-benzo[d][1,2,3]triazol-1-yl-methoxy) |
| phenyl | -n-hexyl- | O | 4-(phenylethoxy) |
| phenyl | -n-hexyl- | O | 4-(4-fluoro-phenoxy) |
| phenyl | -n-hexyl- | O | 4-(pyrimidin-4-yl-methoxy) |
| phenyl | -n-hexyl- | O | 4-(N-methyl-N-benzyl-amino) |
| phenyl | -n-hexyl- | O | 4-(N-methyl-N-(3,4-difluoro-benzyl)-amino) |
| phenyl | -n-hexyl- | O | 4-(N-methyl-N-(pyrid-2-yl-methyl)-amino) |
| phenyl | -n-hexyl- | O | 4-(N-benzyl-N-(t-butoxycarbonyl)-amino) |
| phenyl | -n-hexyl- | O | 4-(N-benzylamino) |
| phenyl | -n-hexyl- | O | 4-(3-cyano-benzyloxy) |
| phenyl | -n-hexyl- | O | 4-(N-(3,4-difluoro-benzyl)-amino) |
| 2-fluoro-pyrid-3-yl | -n-hexyl- | O | 4-phenoxy |
| pyrimidin-5-yl | -n-hexyl- | O | 4-phenoxy |
| phenyl | -n-hexyl- | O | 4-(6-fluoro-pyrid-2-yl-methoxy) |
| phenyl | -n-hexyl- | O | 4-(N-t-butoxycarbonyl-N-(pyrid-3-yl-methyl)-amino) |
| phenyl | -n-hexyl- | O | 4-(N-(pyrid-3-yl-methyl)-amino) |
| phenyl | -n-hexyl- | O | 4-(3-t-butoxycarbonyl-benzyloxy) |
| phenyl | -n-hexyl- | O | 4-(3-carboxy-benzyloxy) |
| 6-fluoro-pyrid-3-yl | -n-hexyl- | O | 4-phenoxy |
| phenyl | -n-hexyl- | S | 4-(3-fluoro-benzyloxy) |
| phenyl | -n-hexyl- | S | 4-(benzyloxy) |
| phenyl | -n-hexyl- | S | 4-phenoxy |
| 3,5-difluoro-phenyl | —O-n-pentyl- | S | 4-phenoxy |
| 3-chloro-phenyl | —O-n-pentyl- | S | 4-phenoxy |
| 6-trifluoro-methyl-pyrid-3-yl | -n-hexyl- | O | 4-phenoxy |
| phenyl | -n-hexyl- | S | 4-(3-methoxycarbonyl-benzyloxy) |
| phenyl | -n-hexyl- | S | 4-(pyrid-3-yl-methoxy) |
| phenyl | -n-hexyl- | S | 4-(pyrid-2-yl-methoxy) |
| phenyl | -n-hexyl- | S | 4-(pyrid-4-yl-methoxy) |
| phenyl | -n-hexyl- | S | 4-(5-methoxycarbonyl-fur-2-yl-methoxy) |
| 5-amino-carbonyl-pyrid-3-yl | -n-hexyl- | O | 4-phenoxy |
| phenyl | —CH=CH—(CH₂)₄— | O | 4-phenoxy |
| phenyl | -n-hexyl- | S | 4-(3-cyano-benzyloxy) |
| phenyl | -n-hexyl- | S | 4-(2-fluoro-benzyloxy) |
| phenyl | -n-hexyl- | S | 4-(3,5-difluoro-benzyloxy) |
| phenyl | -n-hexyl- | S | 4-(2,6-dichloro-pyrid-4-yl-methoxy) |
| phenyl | -n-hexyl- | S | 4-(3-dimethylamino-carbonyl-benzyloxy) |
| phenyl | -n-hexyl- | S | 4-(6-fluoro-pyrid-2-yl-methoxy) |
| phenyl | -n-hexyl- | S | 4-(2-fluoro-pyrid-4-yl-methoxy) |
| 4-methyl-thiazol-5-yl | -n-hexyl- | S | 4-(3-fluoro-benzyloxy) |
| phenyl | -n-hexyl- | S | 4-(pyrid-4-yl-N-oxide)-methoxy- |
| 6-(methyl-carbonyl-amino)-pyrid-3-yl | -n-hexyl- | S | 4-(3-fluoro-benzyloxy) |
| 6-fluoro-pyrid-3-yl | -n-hexyl- | S | 4-(pyrid-4-yl-methoxy) |
| phenyl | -n-hexyl- | S | 4-(3-fluoro-pyrid-4-yl-methoxy) |
| phenyl | -n-hexyl- | S | 4-(6-bromo-pyrid-2-yl-methoxy) |
| phenyl | -n-hexyl- | S | 4-(6-cyano-pyrid-2-yl-methoxy) |
| phenyl | -n-hexyl- | S | 4-(6-chloro-pyrid-2-yl-methoxy) |
| 6-fluoro-pyrid-3-yl | -n-hexyl- | S | 4-(3-fluoro-benzyloxy) |
| 4-methyl-thiazol-5-yl | -n-hexyl- | S | 4-(pyrid-4-yl-methoxy) |
| 6-fluoro-pyrid-3-yl | -n-hexyl- | S | 4-(pyrid-2-yl-methoxy) |
| 6-fluoro-pyrid-3-yl | -n-hexyl- | S | 4-(2-fluoro-pyrid-4-yl-methoxy) |

-continued

| R¹ | L¹ | X | —L²—R⁵ |
|---|---|---|---|
| 6-fluoro-pyrid-3-yl | -n-hexyl- | S | 4-(2-chloro-pyrid-4-yl-methoxy) |
| 6-fluoro-pyrid-3-yl | -n-hexyl- | S | 4-(3-methoxycarbonyl-benzyloxy) |
| phenyl | -n-hexyl- | O | 4-(benzyl-sulfonyl) |
| phenyl | -n-hexyl- | S | 4-(2-chloro-pyrid-4-yl-methoxy) |
| phenyl | -n-hexyl- | S | 4-(2-methyl-pyrid-4-yl-methoxy) |
| phenyl | -n-hexyl- | S | 4-(5-fluoro-pyrid-3-yl-methoxy) |
| pyrimid-2-yl | —NH-n-pentyl- | O | 4-(benzyloxy) |
| phenyl | -n-hexyl- | O | 4-phenoxy | and pharmaceutically acceptable salts thereof.

11. A compound as in claim 1, wherein X is O, selected from the group consisting of

| R¹ | L¹ | A |
|---|---|---|
| phenyl | -n-hexyl- | benzo[d][1,3]dioxol-5-yl |
| phenyl | -n-hexyl- | 6-(2,3-dihydropyrrolo[2,1-b]quinazolin-9-one) |
| phenyl | -n-hexyl- | naphthy-2-yl |
| 3-fluoro-phenyl | -n-hexyl- | naphthy-2-yl |
| 4-fluoro-phenyl | -n-hexyl- | naphthy-2-yl |
| 3-methoxy-phenyl | -n-hexyl- | naphthy-2-yl |
| phenyl | -n-pentyl- | naphthy-2-yl |
| 4-biphenyl | -n-pentyl- | naphthy-2-yl |
| 4-fluoro-phenyl | -n-pentyl- | naphthy-2-yl |
| phenyl | —O-n-pentyl- | naphthy-2-yl |
| 3-fluoro-phenyl | —O-n-pentyl- | naphthy-2-yl |
| phenyl | -n-hexyl- | dibenzo[b,e][1,4]dioxin-2-yl |
| 3-fluoro-phenyl | —O-n-pentyl- | dibenzo[b,e][1,4]dioxin-2-yl |
| phenyl | -n-hexyl- | 3-pyridyl |
| phenyl | -n-hexyl- | 4-pyridyl | and pharmaceutically acceptable salts thereof.

12. A pharmaceutical composition comprising a pharmaceutically acceptable carrier and a compound of claim 1.

13. A pharmaceutical composition made by mixing a compound of claim 1 and a pharmaceutically acceptable carrier.

14. A process for making a pharmaceutical composition comprising mixing a compound of claim 1 and a pharmaceutically acceptable carrier.

15. A method of treating a disorder mediated by the endothelial lipase, comprising administering to a subject in need thereof a therapeutically effective amount of the compound of claim 1, wherein the disorder mediated by the endothelial lipase is selected from the group consisting of atherosclerosis, dyslipidemia, low HDL and high LDL.

16. A method of treating a disorder selected from the group consisting of atherosclerosis, dyslipidemia, low HDL and high LDL comprising administering to the subject in need thereof a therapeutically effective amount of the composition of claim 12.

17. A method of treating a condition selected from the group consisting of atherosclerosis, dyslipidemia, low HDL and high LDL comprising administering to the subject in need thereof a therapeutically effective amount of the compound of claim 1.

* * * * *